(12) United States Patent
Liu et al.

(10) Patent No.: US 11,555,054 B2
(45) Date of Patent: *Jan. 17, 2023

(54) RAPADOCINS, INHIBITORS OF EQUILIBRATIVE NUCLEOSIDE TRANSPORTER 1 AND USES THEREOF

(71) Applicant: The Johns Hopkins University, Baltimore, MD (US)

(72) Inventors: Jun Liu, Baltimore, MD (US); Jingxin Wang, Baltimore, MD (US); Zhaoli Sun, Baltimore, MD (US); Sam Hong, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/003,940

(22) Filed: Aug. 26, 2020

(65) Prior Publication Data

US 2020/0392182 A1    Dec. 17, 2020

Related U.S. Application Data

(63) Continuation of application No. 16/073,746, filed as application No. PCT/US2017/016494 on Feb. 3, 2017, now Pat. No. 10,774,110.

(60) Provisional application No. 62/291,428, filed on Feb. 4, 2016.

(51) Int. Cl.
| | |
|---|---|
| *C07K 5/103* | (2006.01) |
| *C07D 498/18* | (2006.01) |
| *C07D 519/00* | (2006.01) |
| *A61K 47/54* | (2017.01) |
| *A61K 38/07* | (2006.01) |

(52) U.S. Cl.
CPC ............ *C07K 5/1008* (2013.01); *A61K 38/07* (2013.01); *A61K 47/545* (2017.08); *C07D 498/18* (2013.01); *C07D 519/00* (2013.01)

(58) Field of Classification Search
None
See application file for complete search history.

(56) References Cited

U.S. PATENT DOCUMENTS

| | | | |
|---|---|---|---|
| 5,212,155 A * | 5/1993 | Calne | A61P 37/00 514/21.1 |
| 5,457,194 A | 10/1995 | Luly et al. | |
| 5,527,907 A | 6/1996 | Or et al. | |
| 5,798,355 A | 8/1998 | Steiner et al. | |
| 6,984,635 B1 | 1/2006 | Schreiber et al. | |
| 7,056,935 B2 | 6/2006 | Steiner et al. | |
| 7,358,235 B2 | 4/2008 | Puetz et al. | |
| 7,803,808 B2 | 9/2010 | Gregory et al. | |
| 7,989,395 B2 | 8/2011 | Morgan et al. | |
| 8,642,215 B2 | 2/2014 | Kim et al. | |
| 8,956,825 B2 | 2/2015 | Weisbart | |
| 9,250,237 B2 | 2/2016 | Liu et al. | |
| 9,840,518 B2 | 12/2017 | Hird et al. | |
| 9,989,535 B2 | 6/2018 | Verdine et al. | |
| 10,466,249 B2 | 11/2019 | Verdine et al. | |
| 10,533,016 B2 | 1/2020 | Verdine et al. | |
| 10,662,220 B2 * | 5/2020 | Liu | C07K 5/10 |
| 10,774,110 B2 * | 9/2020 | Liu | A61K 9/0019 |
| 2002/0052410 A1 | 5/2002 | Steiner et al. | |
| 2006/0003362 A1 | 1/2006 | Zerangue | |
| 2008/0292618 A1 | 11/2008 | Weisbart | |
| 2008/0306098 A1 | 12/2008 | Mutz et al. | |

(Continued)

FOREIGN PATENT DOCUMENTS

| | | |
|---|---|---|
| JP | 8-333256 H | 12/1996 |
| JP | 2011-524413 | 9/2011 |

(Continued)

OTHER PUBLICATIONS

Choi et al. "Structure of the FKBP12-Rapamycin Complex Interacting with the Binding Domain of Human FRAP" Science 273:239-242 (1996).

(Continued)

*Primary Examiner* — Sudhakar Katakam
*Assistant Examiner* — Zachary J Miknis
(74) *Attorney, Agent, or Firm* — DLA Piper LLP (US)

(57) ABSTRACT

A compound of Formula I,

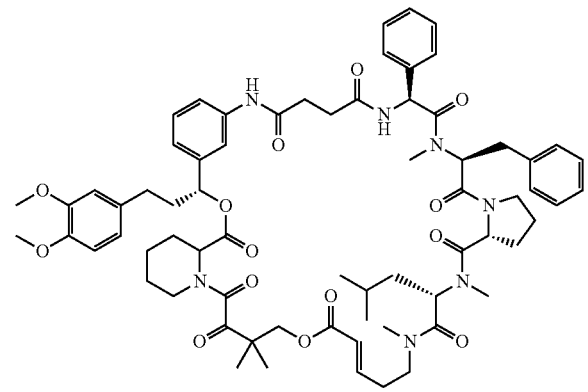

and its analogs are provided. Compositions that include Formula I can be used to inhibit human equilibrative nucleoside transporter 1, increase adenosine signaling and produce effects that include increasing antiviral activity, increasing antiparasitic activity, increasing alcohol tolerance, decreasing pain protecting from ischemia as well as many other conditions.

3 Claims, 4 Drawing Sheets

(56) References Cited

U.S. PATENT DOCUMENTS

| | | |
|---|---|---|
| 2009/0253732 A1 | 10/2009 | Gregory et al. |
| 2014/0073581 A1 | 3/2014 | Liu et al. |
| 2014/0206624 A1 | 7/2014 | Sykes et al. |
| 2015/0018340 A1 | 1/2015 | Gopalakrishnan et al. |
| 2015/0050356 A1 | 2/2015 | Desai et al. |
| 2015/0203512 A1 | 7/2015 | Reger et al. |
| 2017/0305926 A1 | 10/2017 | Hird et al. |
| 2019/0224274 A1 | 7/2019 | Dawson et al. |
| 2020/0040004 A1 | 2/2020 | Liu et al. |
| 2021/0214390 A1* | 7/2021 | Liu ................ A61K 31/353 |

FOREIGN PATENT DOCUMENTS

| | | |
|---|---|---|
| JP | 6891183 B2 | 6/2021 |
| WO | WO 1996/40140 | 12/1996 |
| WO | WO 2004/093798 | 11/2004 |
| WO | WO 2010/004304 | 1/2010 |
| WO | WO 2012/075048 | 6/2012 |
| WO | WO 2014/201405 | 12/2014 |
| WO | WO 2018/045250 | 3/2017 |
| WO | WO 2017/136708 A1 | 8/2017 |
| WO | WO 2017/136717 | 8/2017 |
| WO | WO 2017/136731 A1 | 8/2017 |
| WO | WO 2019/064182 | 4/2019 |

OTHER PUBLICATIONS

Extended European Search Report dated Jul. 16, 2019, regarding EP 17 74 8270.

Guo, Zufeng et al.: "Rapamycin-inspired macrocycles with new target specificity"; Nature Chemistry, vol. 11, No. 3, Dec. 10, 2018, pp. 254-263, XP036706998, ISSN: 1755-4330, DOI: 10.1038/S41557-018-0187-4. [retrieved on Dec. 10, 2018].

Huang, M. et al.: "Inhibition of Nucleoside Transport by Protein Kinase Inhibitors"; J. Pharmacology and Experimental Therapeutics, vol. 304, No. 2, Jan. 1, 2003, pp. 753-760, XP008036291, ISSN: 0022-3565, DOI: 10.1124/JPET.102.044214.

Nakanishi, T. "Drug Transporters as Targets for Cancer Chemotherapy," Cancer Genomics & Proteomics (2007), 4:241-254.

Bauerle et al., "Adenosine Generation and Signaling during Acute Kidney Injury", J Am Soc Nephrol, 2011, 22:14-20.

Chen et al., "Adenosine receptors as drug targets—what are the challenges?", Nat Rev Drug Discov., Apr. 2013, 12(4):265-286.

Choi et al., "The type 1 equilibrative nucleoside transporter regulates ethanol intoxication and preference", Nature Neuroscience, Aug. 2004, 7(8):855-861.

Grenz et al., "Equilibrative nucleoside transporter 1 (ENT1) regulates postischemic blood flow during acute kidney injury in mice", J Clin Invest., 2014, 124(6):2807-2807.

Grenz et al., "The Reno-Vascular A2B Adenosine Receptor Protects the Kidney from Ischemia", PLoS Medicine, Jun. 2008, 5(6):968-986.

Griffith et al., "Nucleoside and nucleobase transport systems of mammalian cells", Biochimica et Biophysica Acta, 1996, 1286:153-181.

JP Office Action in Japanese Application No. 2018-540114, dated Jan. 26, 2021, 8 pages (with English translation).

Li et al., "Inhibition of human equilibrative nucleoside transporters by dihydropyridine-type calcium channel antagonists", European Journal of Pharmacology, 2007, 568:75-82.

Lin et al., "Synthesis, Flow Cytometric Evaluation, and Identification of Highly Potent Dipyridamole Analogues as Equilibrative Nucleoside Transporter 1 Inhibitors", J. Med. Chem., 2007, 50:3906-3920.

Melendez et al., "Last call for adenosine transporters", Nature Neuroscience, Aug. 2004, 7(8): 795-796.

Mohamadnejad et al., "Adenosine Inhibits Chemotaxis and Induces Hepatocyte-Specific Genes in Bone Marrow Mesenchymal Stem Cells", Hepatology, Mar. 2010, 51(3):963-973.

Passer et al., "Identification of then ENT1 antagonists dipyridamole and dilazep as amplifiers of oncolytic herpes simplex virus-1 replication", Cancer Res., May 2010, 70(10):3890-3895.

Pennycooke et al., "Differential Expression of Human Nucleoside Transporters in Normal and Tumor Tissue", Biochemical and Biophysical Research Communications, 2001, 280:951-959.

Sachdeva et al., "Adenosine and its receptors as therapeutic targets: An overview", Saudi Pharmaceutical Journal, 2013, 21:245-253.

Tromp et al., "Inhibition of Nucleoside Transport by New Analogues of 4-Nitrobenzylthiosine: Replacement if the Ribose Moiety by Substituted Benzyl Groups", J. Med. Chem., 2004, 47:5441-5450.

Visser et al., "Residues 334 and 338 in Transmembrane Segment 8 of Human Equilibrative nucleoside Transporter 1 Are Important Determinants of Inhibitor Sensitivity, Protein Folding, and Catalytic Turnover", Journal of Biological Chemistry, May 2007, 282(19):14148-14157.

Wen et al., "Adenosine Signaling Good or Bad in Erectile Function?" Arterioscler Thromb Vase Biol, Apr. 2012, 32:845-850.

Xu et al., "ENT1 Inhibition Attenuates Epileptic Seizure Severity Via Regulation of Glutamatergic Neurotransmission", Neuromol Med, 2015, 17:1-11.

Zimmerman et al., "Equilibrative nucleoside transporter (ENT)-1-dependent elevation of extracellular adenosine protects the liver during ischemia and reperfusion", Hepatology, Nov. 2013, 58(5):1766-1778.

Panchenko et al., "Prediction of functional sites by analysis of sequence and structure conservation", Protein Science, 2004, 13:884-892.

Amigo: A Novel Tag Analysis Methodology That Enables Detection of Molecules from DNAEncoded Chemical Libraries. SLAS Discovery 2018, 23(5), 397-404. 10.1177/2472555217753840.

Arico-Muendel, From haystack to needle: finding value with DNA encoded library technology at GSK MedChemComm, (2016) 7(10): 1898-1909.

Bao, Krylov Predicting Electrophoretic Mobility of Protein-Ligand Complexes for Ligands from DNA-Encoded Libraries of Small Molecules Anal. Chem., (2016) 88 (10):5498-5506.

Blaksjaer, Fidelity by design: Yoctoreactor and binder trap enrichment for smallmolecule DNA-encoded libraries and drug discovery. Curr Opin Chem Biol. 2015;26:62-71. doi:10.1016/j.cbpa.2015.02.003.

Brown et al., Retrospective on Cholesterol Homeostasis: The Central Role of Scap. Annu Rev Biochem. 2018;87:783-807. doi:10.1146/annurev-biochem-062917-011852.

Buller et al. Design and synthesis of a novel DNAencoded chemical library using Diels-Alder cycloadditions. Bioorg Med Chem Lett. 2008;18(22):5926-5931. doi:10.1016/j.bmc1.2008.07.038.

Buller et al. Drug Discovery with DNA-Encoded Chemical Libraries Bioconjugate Chem. (2010) 21, 1571-80.

Buller, High-throughput sequencing for the identification of binding molecules from DNA-encoded chemical libraries Bioorg Med Chem Lett. (2010) 15;20(14):4188-92.

Castanon, Design and Development of a Technology Platform for DNA-Encoded Library Production and Affinity Selection [published correction appears in SLAS Discov. Jun. 2018;23 (5):489], SLAS Discov. 2018;23(5):387-396. doi:10.1177/2472555217752091.

Chakraborty et al: "Design and synthesis of a rapamycin-based high affinity binding FKPB12 ligand"; Chemistry & Biology, Mar. 1995, 2, 157-161.

Chan et al.,. Novel selection methods for DNA-encoded chemical libraries. Curr Opin Chem Biol. 2015;26:55-61. doi:10.1016/j.cbpa.2015.02.010.

Clark et al. Design, synthesis and selection of DNA-encoded small-molecule libraries [published correction appears in Nat Chem Biol. Oct. 2009;5(10):772], Nat Chem Biol. 2009;5(9):647-654. doi:10.1038/nchembio.211.

Clark, Selecting chemicals: the emerging utility of DNA-encoded libraries Curr Opin Chem Biol. (2010) 14(3):396-403.

Connors et al. DNA-encoded chemical libraries of macrocycles. Curr Opin Chem Biol. 2015;26:42-47. doi:10.1016/j.cbpa.2015.02.004.

(56) References Cited

OTHER PUBLICATIONS

Cuozzo et al. Discovery of a Potent BTK Inhibitor with a Novel Binding Mode by Using Parallel Selections with a DNA-Encoded Chemical Library BioChem (2017), 18(9):864-71.
Decurtins et al. Automated screening for small organic ligands using DNA-encoded chemical libraries. Nat Protoc. 2016;11(4):764-780. doi:10.1038/nprot.2016.039.
Deng et al. Discovery, SAR, and X-ray Binding Mode Study of BCATm Inhibitors from a Novel DNA-Encoded Library Bioconjug Chem. (2017) 20;28(9):2293-2301.
Denton, Crosslinking of DNA-linked ligands to target proteins for enrichment from DNA-encoded libraries. Medchemcomm. 2016;7(10):2020-2027. doi:10.1039/C6MD00288A.
Ding et al. Discovery of Potent and Selective Inhibitors for ADAMTS-4 through DNA-Encoded Library Technology (ELT). ACS Med Chem Lett. 2015;6(8):888-893. Published Jul. 7, 2015. doi:10.1021/acsmedchemlett.5b00138.
Ding, Design and Synthesis of Biaryl DNA-Encoded Libraries ACS Comb Sci. (2016) 10;18(10):625-629.
Eidam et al., Analysis of the productivity of DNA encoded libraries MedChemComm, (2016) 7(7): 1323-1331.
Estevez, A carbohydrate-derived trifunctional scaffold for DNA-encoded Libraries Tetrahedron: Asymmetry. (2017) 28:837-842.
European Search Report and Search Opinion Received for EP Application No. 17748264.3, dated Aug. 16, 2019, 18 pages.
Franzini et al. Identification of structure-activity relationships from screening a structurally compact DNA-encoded chemical library. Angew Chem Int Ed Engl. 2015;54(13):3927-3931. doi:10.1002/anie.201410736.
Franzini et al. Interrogating target-specificity by parallel screening of a DNA-encoded chemical library against closely related proteins Chem Commun. (2015) 11;51(38):8014-16.
Franzini et al., DNA-Encoded Chemical Libraries: Advancing beyond Conventional Small-Molecule Libraries Acc Chem Res. (2014) 15;47(4):1247-55.
Franzini et al., Evaluation and Optimization of Modification Reactions of Oligonucleotides with Amines and Carboxylic Acids for the Synthesis of DNA-Encoded Chemical Libraries Bioconjug Chem. (2014) 20;25(8):1453-61.
Gartner et al., DNA-templated organic synthesis and selection of a library of macrocycles. Science. 2004;305(5690):1601-1605. doi:10.1126/science.1102629.
Halford, Breakthroughs with Bar Codes C&EN, (2017) 95(25): 28-33.
Harris et al. DNA-Encoded Library Screening Identifies Benzo[b][1,4]oxazepin-4-ones as Highly Potent and Monoselective Receptor Interacting Protein 1 Kinase Inhibitors. J Med Chem. 2016; 59(5):2163-2178. doi:10.1021/acs.jmedchem.5b01898.
Hong, "Rapamycin-based macrocyclic library development and Equilibrative Nucleoside Transporter 1 (ENT1) inhibition", A dissertation submitted to John Hopkins University in conformity with the requiregments for the degree of Doctor of Philosophy, Jun. 2016, 134 pages.
Huang et al.: "Inhibition of Nucleoside Transport By Protein Kinase Inhibitors"; J. Pharmacology and Experimental Therapeutics, vol. 304, No. 2, Jan. 1, 2003, pp. 753-760, XP008036291, ISSN: 0022-3565, DOI: 10.1124/JPET.102.044214.
JP Office Action in Japanese Application No. 2018-540115, dated Jan. 12, 2021, 8 pages (with English translation).
JP Office Action dated Oct. 27, 2020, regarding JP 2018-540102.
Keefe et al., Chemical ligation methods for the tagging of DNA-encoded chemical libraries. Curr Opin Chem Biol. 2015;26:80-88. doi:10.1016/j.cbpa.2015.02.015.
Kleiner et al., Small-molecule discovery from DNA-encoded chemical libraries Chem Soc Rev. (2011) 40(12): 5707-17.
Krall et al., Small targeted cytotoxics: current state and promises from DNA-encoded chemical libraries. Angew Chem Int Ed Engl. 2013;52(5):1384-1402. doi:10.1002/anie.201204631.
Kuai et al., Randomness in DNA encoded library selection data can be modeled for more reliable enrichment calculation. SLAS Discov. 2018;23(5):405-416.
Li et al. Quantitative PCR is a Valuable Tool to Monitor the Performance of DNA-Encoded Chemical Library Selections. Chembiochem. 2017;18(9):848-852. doi:10.1002/cbic.201600626.
Lim, Making ring compounds for DNA encoded libraries C&EN, (2017) 95 (29):10.
Machutta et al. Prioritizing multiple therapeutic targets in parallel using automated DNA—encoded library screening. Nat Commun 8,16081(2017). https://doi.org/10.1038/ncomms16081.
Mannocci et al. High-throughput sequencing allows the identification of binding molecules isolated from DNA-encoded chemical libraries. Proc Natl Acad Sci USA. 2008; 105(46): 17670-17675. doi:10.1073/pnas.0805130105.
Mannocci et al., 20 years of DNA-encoded chemical libraries Chem. Commun. (2011) 47:12747-53.
Mannocci et al., Isolation of Potent and Specific Trypsin Inhibitors from a DNA-Encoded Chemical Library Bioconjugate Chem. (2010) 21, 1836-41.
Melkko et al. Encoded self-assembling chemical libraries. Nat Biotechnol. 2004;22(5):568-574 doi:10.1038/nbt961.
Nakanishi "Drug Transporters as Targets for Cancer Chemotherapy," Cancer Genomics & Proteomics (2007), 4:241-254.
Neri et al.,"DNA-Encoded Chemical Libraries: A Selection System Based on Endowing Organic Compounds with Amplifiable Information", Annu Rev Biochem. 2018;87:479-502. doi:10.1146/annurev-biochem-062917-012550.
Neri, Twenty-five Years of DNA-Encoded Chemical Libraries Chembiochem. (2017) 4;18(9):827-828.
PCT International Preliminary Report on Patentability received for PCT Patent Application No. PCT/US17/16481, dated Aug. 16, 2018, 7 pages.
PCT International Search Report and Written Opinion in International Application No. PCT/US2020/53486, dated Jan. 8, 20201, 8 pages.
PCT International Search Report and Written Opinion in International Application No. PCT/US2020/53549, dated Feb. 4, 2021, 9 pages.
PCT International Search Report and Written Opinion received for PCT Patent Application No. PCT/US17/16481, dated Apr. 21, 2017, 8 pages.
Salamon, Chemical Biology Probes from Advanced DNA-encoded Libraries ACS Chem Biol. (2016) 19;11 (2):296-307.
Satz et al. Analysis of Current DNA Encoded Library Screening Data Indicates Higher False Negative Rates for Numerically Larger Libraries ACS Comb Sci. (2017) 10;19(4):234-238.
Satz, DNA Compatible Multistep Synthesis and Applications to DNA Encoded Libraries Bioconjug Chem. (2015) 19;26(8):1623-32.
Satz, DNA Encoded Library Selections and Insights Provided by Computational Simulations ACS Chem Biol. (2016) 16;10(10):2237-45.
Satz, Simulated Screens of DNA Encoded Libraries: The Potential Influence of Chemical Synthesis Fidelity on Interpretation of Structure-Activity Relationships CS Comb. Sci. (2016) 18 (7):415-424.
Scheuermann et al., DNA-Encoded Chemical Libraries for the Discovery of MMP-3 Inhibitors Bioconjugate Chem. 2008, 19, 778—785.
Scheuermann et al., Dual-pharmacophore DNA-encoded chemical libraries Curr Opin Chem Biol. (2015) 26:99-103.
Shi et al. Recent advances on the encoding and selection methods of DNA-encoded chemical library. Bioorg Med Chem Lett. 2017;27(3):361-369. doi:10.1016/j.bmcl.2016.12.025.
Shi et al.,"Selecting a DNA-Encoded Chemical Library against Non-immobilized Proteins Using a "Ligate-Cross-Link-Purify" Strategy", Bioconjugate Chemistry, 2017, 28:2293-2301.
Skopic, Acid- and Au(I)-mediated synthesis of hexathymidine-DNA-heterocycle chimeras, an efficient entry to DNA-encoded libraries inspired by drug structures Chem Sci. (2017) 1;8(5):3356-3361.
Skopic, Design and synthesis of DNA-encoded libraries based on a benzodiazepine and a pyrazolopyrimidine scaffold MedChemComm, (2016) 7(10): 1957-1965.

(56) References Cited

OTHER PUBLICATIONS

Upadhyaya et al.: "Inhibition of Ras Signaling by Blocking Ras-Effector Interactions with Cyclic Peptides"; Angewandte Chemie International, 2015, 54, 7602-7606.
Wrenn et al., Chemical Evolution as a Tool for Molecular Discovery Annu. Rev. Biochem. (2007) 76:331-49.
Wu et al.: "Creating diverse Target Binding Surfaces on FKBP12: Synthesis and Evaluation of a Rapamycin Analogue Library"; ACS Combinatorial Science, 2011, 13, 486-495.
Wu et al.: "Inhibition of Ras-Effector Interaction by Cyclic Peptides"; Medchemcomm, Feb. 1, 2013, 4(2), 378-382.
Xia et al., Development and design of the tertiary amino effect reaction for DNA-encoded library synthesis. MedChemComm 2016;7(7),1316-1322.
Yuen et al., Achievements, Challenges, and Opportunities in DNA Encoded Library Research: An Academic Point of View Chembiochem. (2017) 4;18(9):829-836.
Zhang, "Protein Tyrosine Phosphatases: Structure and Function, Substrate Specificity, and Inhibitor Development", Annu. Rev. Pharmacol. Toxicol., 42:209-234, 2002.
Zimmerman et al., DNA-encoded chemical libraries: foundations and applications in lead discovery Drug Discov. Today (2016) 21(11):1828-1834.
Zimmerman et al. Hit-Validation Methodologies for Ligands Isolated from DNA-Encoded Chemical Libraries. Chembiochem. 2017;18(9):853-857. doi:10.1002/cbic.201600637.
JP Office Action in Japanese Application No. JP-A-2021-088242, dated Apr. 5, 2022, 6 pages (with English translation).

\* cited by examiner

RAPADOCINS, INHIBITORS OF EQUILIBRATIVE NUCLEOSIDE TRANSPORTER 1 AND USES THEREOF

CROSS-REFERENCE TO RELATED APPLICATIONS

This application is continuation application of U.S. application Ser. No. 16/073,746 filed Jul. 27, 2018, now pending; which is a 35 USC § 371 National Stage application of International Application No. PCT/US2017/016494 filed Feb. 3, 2017, now expired; which claims the benefit under 35 USC § 119(e) to U.S. Application Ser. No. 62/291,428 filed Feb. 4, 2016, now expired. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under CA174428 awarded by the National Institutes of Health. The government has certain rights in the invention.

BACKGROUND OF THE INVENTION

Field of the Invention

The present invention relates generally to small molecule compounds and more specifically to the use of such compounds for inhibiting human equilibrative nucleoside transporter 1 (ENT1).

Background Information

Transporter proteins are involved in the cellular uptake of various molecules into and/or through cells. Carrier-mediated transport systems use proteins that are anchored to the cell membrane, typically by a plurality of membrane-spanning domains and function by transporting their substrates via active or passive mechanisms. Carrier-mediated transport systems are involved in the active or non-active, facilitated transport of many important nutrients such as vitamins, sugars, and amino acids. Carrier-mediated transporters are also present in organs such as the liver and kidney, in which the proteins are involved in the excretion or re-absorption of circulating compounds. Polar or hydrophilic compounds typically diffuse poorly across the lipid bilayers that constitute cellular membranes. For many small molecules (e.g., amino acids, di- and tripeptides, monosaccharides, nucleosides and water-soluble vitamins) there exist specific carrier-mediated transporters for active transport of the solute molecules across biological membranes.

The uptake or release of physiological nucleosides and many of their synthetic analogs by mammalian cells occurs primarily by means of specific carrier-mediated transporters known as nucleoside transporters. Nucleoside transporters have been classified into two categories: (i) equilibrative (facilitated diffusion) and (ii) concentrative (secondary active) sodium-dependent. Two equilibrative transport systems with similar broad substrate specificities have been identified and designated as the es (equilibrative sensitive) and ei (equilibrative insensitive) transporters, on the basis of their sensitivity or insensitivity to inhibition by nitrobenzyl-thioinosine (NBMPR, 1), respectively.

Specific transporters are required for the permeation of nucleosides across cell membranes. Among the family of nucleoside transporters the equilibrative nucleoside transporters (ENTs) are the most broadly expressed and four human ENTs have been identified in humans: hENT-1, hENT-2, hENT-3 and hENT-4. The most thoroughly characterized are hENT-1 and hENT-2 which are cell surface proteins and are broadly selective for both purine and pyrimidine nucleosides. They can be distinguished from each other by their sensitivities to inhibition by nitrobenzylmercaptopurine riboside (NBMPR). ENT1 is potently inhibited by nanomolar concentrations of NBMPR and is therefore also called a NBMPR sensitive equilibrative nucleoside transport protein. ENT2 is insensitive to nanomolar concentrations of NBMPR, but can be inhibited by higher (micromolar) concentrations of NBMPR and is therefore also referred to as a NBMPR insensitive equilibrative nucleoside transport protein (iENTP) (see Griffith et al., Biochim. Bioph. Acta 1286:153-181 (1986)).

Human equilibrative nucleoside transporter 1 (ENT1) is encoded by the SLC29a1 gene. The gene is a member of the equilibrative nucleoside transporter family. The gene encodes a transmembrane glycoprotein that localizes to the plasma and mitochondrial membranes and mediates the cellular uptake of nucleosides from the surrounding medium. The protein is categorized as an equilibrative (as opposed to concentrative) transporter that is sensitive to inhibition by nitrobenzylmercaptopurine ribonucleoside (NBMPR). Nucleoside transporters are required for nucleotide synthesis in cells that lack de novo nucleoside synthesis pathways, and are also necessary for the uptake of cytotoxic nucleosides used for cancer and viral chemotherapies.

Adenosine is an endogenous purine nucleoside that is particularly released in pathophysiological conditions like ischemia, inflammation and pain. Under these circumstances it plays an important neuro- and immunomodulatory role. Adenosine administration is analgesic in various nociceptive modalities in humans. Because of the short half-life of adenosine and side-effects caused by its administration, there has been considerable interest in finding ways to reinforce the effects of endogenous adenosine. Inhibition of the ENT1 blocks uptake of adenosine into cells and could enhance its beneficial effects.

SUMMARY OF THE INVENTION

In one embodiment, the invention provides compounds that include the following: Formula I, Formula II, Formula III, Formula IV, Formula V, Formula VI, Formula VII, Formula VIII, Formula IX, Formula X, Formula XI, XII JW95-1, JW95-2, JW95-3, JW95-4, JW95-5, JW95-6, JW95-7, JW95-8, JW95-9, JW95-10, JW95-11, JW95-12, JW95-13, JW95-14, JW95-15, JW95-16, JW95-17, JW95-18, JW95-19, JW95-20, JW95-21, JW95-22, JW95-23, JW95-24, JW95-25, 95-15-1, 95-15-2, 95-15-3, 95-15-4, 95-15-5, 95-15-6, 95-15-7, 95-15-8, 95-15-9, 95-15-10, 95-15-11, 95-15-12, 95-15-13, 95-15-14, 95-15-15, 95-15-16, 95-15-17, 95-15-18, 95-15-19, 95-15-20, 95-15-21, 95-15-22, 95-15-23, 95-15-13-2, 95-15-13-3, 95-15-13-4, 95-15-13-5, 95-15-13-6, 95-15-13-7, 95-15-13-8, 95-15-13-9, 95-15-13-10, 95-15-13-11, 95-15-13-12, 95-15-13-13, 95-15-13-14, 95-15-13-15 and JW95S2Biotin. The compounds are illustrated in the structures provided herein.

Another embodiment of the present invention is to provide a method of inhibiting human equilibrative nucleoside transporter 1 (ENT1) that includes administering to a subject in need thereof an effective amount of compound listed above.

Another embodiment of the present invention is to provide a method of increasing adenosine signaling that includes administering to a subject in need thereof an effective amount of a compound listed above.

Another embodiment of the present invention is to provide a method of increasing adenosine signaling that includes administering to a subject in need thereof an effective amount of a compound listed above. The administering of the aforementioned compound results in one or more of the following effects: increase in antiviral activity, increase in antiparasitic activity, increase in alcohol tolerance, decrease in pain and protection from ischemia, attenuation of epileptic seizure severity, lessening of erectile dysfunction, improvement of liver function, improvement of respiratory disorders, improvement of sepsis, improvement of thrombosis, improvement of hypertension, improvement of inflammatory disorders, improvement of allergies, improvement of cardiac ischemias, improvement of arrhythmias, improvement of Parkinson's disease, improvement of chronic heart failure, improvement of rheumatoid arthritis, improvement of dry eye disease, improvement of chronic plaque type psoriasis, improvement of chronic neuropathological pain and improvement of sickle cell disease.

Another embodiment of the present invention is to provide a compound with the following structure:

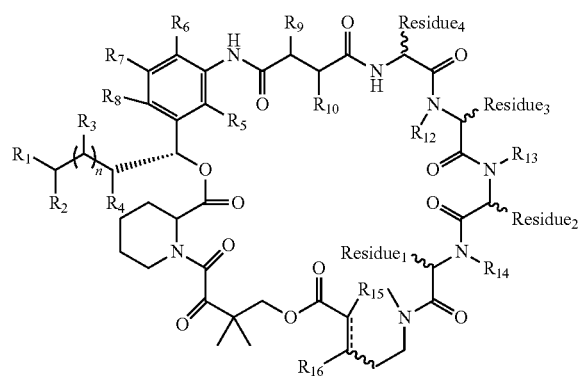

n=0-6

$R_1$:

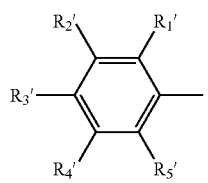

Wherein $R_1'$-$R_5'$=OH, $NH_2$, SH, CN, H, OAc, or OMe individually or in combination.

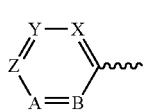

Wherein: A, B, X, Y, Z=C, N, or P either individually or in combination.

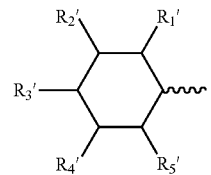

Wherein $R_1'$-$R_5'$=OH, $NH_2$, SH, H, OAc, OMe individually or in combination.

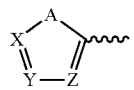

Wherein A, X, Y, or Z=$CH_n'$ (n'=0-2), O, N, S, wherever appropriate, individually or in combination.

$R_2$-$R_4$: H, methyl, ethyl, propyl, isopropyl, phenyl, OH, $NH_2$, SH, CN, individually or in combination.

$R_5$-$R_8$: methyl, ethyl, propyl, isopropyl, phenyl, OH, $NH_2$, SH, CN, individually or in combination.

$R_9$=OH, $NH_2$, SH, CN, H;

$R_{10}$=OH, $NH_2$, SH, CN, H.

$R_{11-14}$=H or Me.

$R_{15}$=OH, $NH_2$, SH, CN, H;

$R_{16}$=OH, $NH_2$, SH, CN, H.

The bond between the carbons bearing $R_{15}$ and $R_{16}$ can be either a single or a double bond in either E or Z configuration.

wherein residues 1-4 can be any amino acid building block listed in below or its modified version

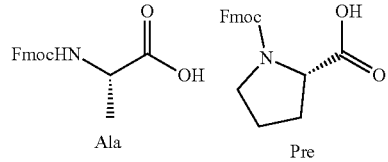

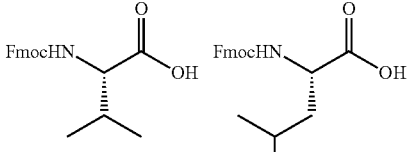

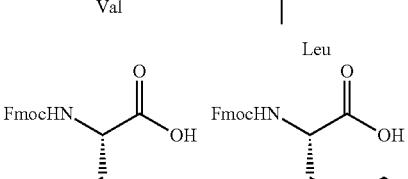

-continued

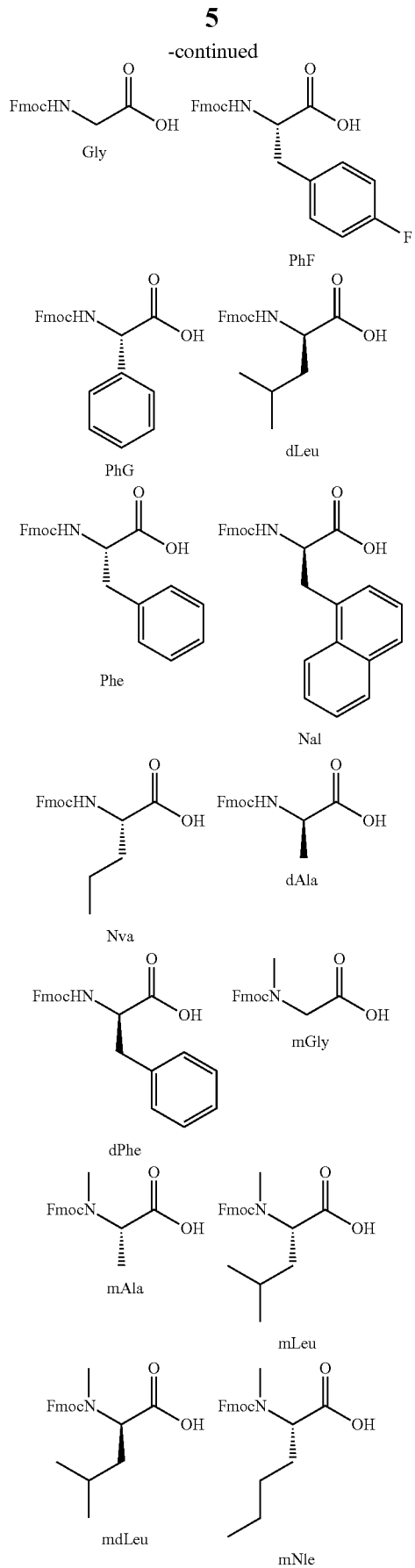

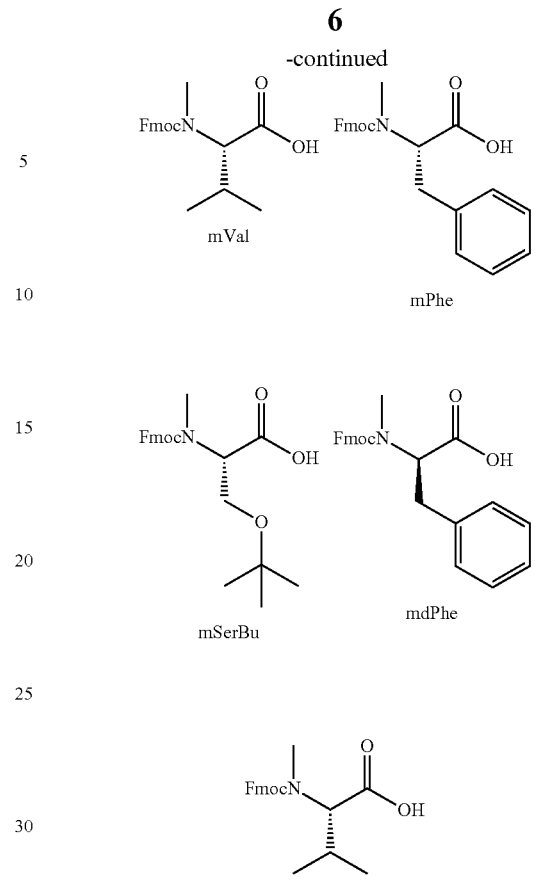

Another embodiment of the present invention is to use the foregoing compound in the methods discussed above.

Other aspects and advantages of the invention will be apparent from the following description and the appended claims.

DETAILED DESCRIPTION OF THE INVENTION

Figure 1:
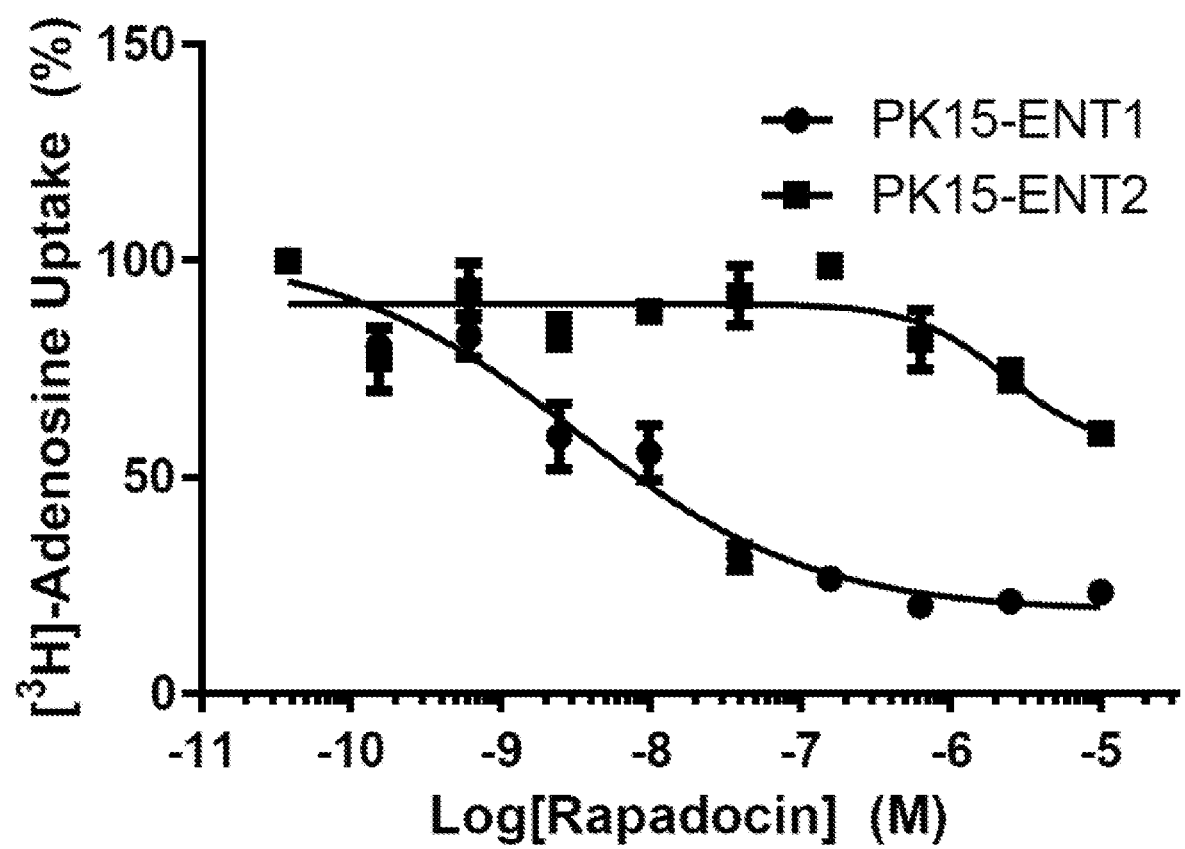
FIG. 1. Rapadocin inhibits $^3$H-Adenosine uptake by specifically inhibiting hENT1.

Other aspects and advantages of the invention will be apparent from the following description. Rapadocin Formula I (stylized as Rapadocin or also named JW95) is a synthetic macrocyclic small molecule. Rapadocin specifically inhibits the human equilibrative nucleoside transporter 1 (hENT1 or SLC29a1) with high potency.

Formula I

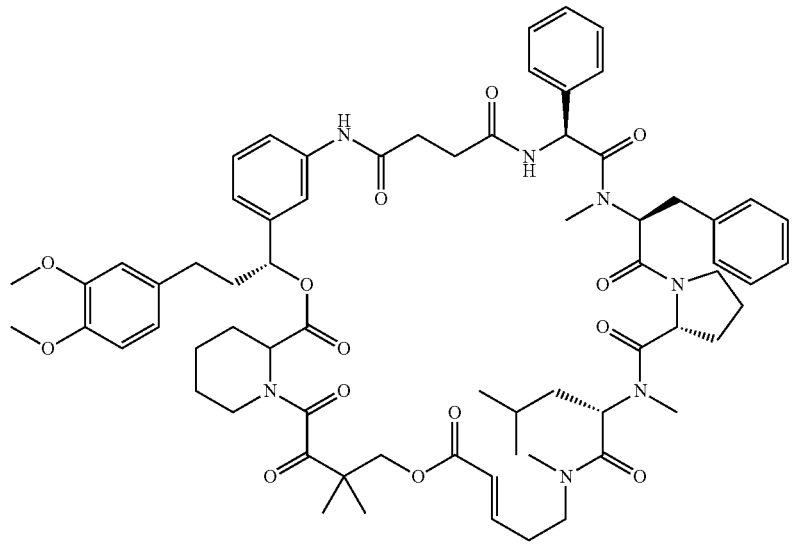

Rapadocin has been shown to be safely tolerated in animals via a kidney ischemia model. Rapadocin is a synthetic macrocycle composed of two 'domains'—a FKBD (FKBP12 binding domain) and a peptide domain. The FKBD can tolerate modifications at the dimethoxy phenyl region, notably to a dihydroxy phenyl analog. The peptidic fragment can tolerate a range of modifications with varying effects on ENT1 inhibition. Notably, the peptidic fragment can tolerate a few important modifications on the N-methyl phenylalanine residue.

The compound of Formula I is soluble up to 10 µM in aqueous solutions and has been shown to resist degradation over 5 days in cell culture media (37° C., 10% Fetal Bovine Serum).

Two different families of nucleoside transporters (NTs) have been characterized: equilibrative nucleoside transporters and concentrative nucleoside transporters. "Equilibrative nucleoside transporters" or "ENTs" refer to transporters that translocate substrate down the substrate's concentration gradient via passive transport or facilitated diffusion. ENT activity does not require a sodium ion (or other ion) gradient and are therefore termed "Na+-independent" transporters. ENTs are categorized into one of two subtypes based on sensitivity to inhibition by nitrobenzylmercaptopurine riboside (NBMBR).

Four members of the ENT family have been cloned and are termed ENT1, ENT2, ENT3, and ENT4. All 4 transport adenosine but differ from each other with respect to their ability to transport other nucleosides or nucleobases. ENT1 is an es subtype transporter. Exemplary polynucleotide sequences encoding human ENT1 include GenBank Accession No. U81375 and GenBank Accession No. AAC51103.1 represents the corresponding amino acid sequence. ENT1 is ubiquitously expressed in human and rodent tissues, although expression levels vary between tissues. ENT1 is known to transport a wide range of purine and pyrimidine nucleosides.

ENT2 is an ei subtype transporter. Exemplary polynucleotide sequences encoding human ENT2 include GenBank Accession No. AF029358 and GenBank Accession No. AAC39526 represents the corresponding amino acid sequence. ENT2 is expressed in a wide range of human and rodent tissues, including vascular endothelium, heart, brain, placenta, thymus, pancreas, prostate, kidney, and muscle, skeletal muscle, cardiac muscle, blood, skin, and ENT2-expressing cancer cells. ENT2-expressing cancer cells include, for example, certain renal tumor cells, breast tumor cells, prostate cancer cells, colon cancer cells, stomach cancer cells, leukemia cells, lung cancer cells, and ovarian cancer cells. Other types of ENT-2 expressing cancer cells are known in the art; (see e.g., Lu X et al., Journal of Experimental Therapeutics and Oncology 2:200-212, 2002, and Pennycooke M et al., Biochemical and Biophysical Research Communications 208, 951-959, 2001). ENT2 exhibits high expression levels in skeletal muscle. ENT2 is also expressed in the membrane of organelles such as the nucleus. ENT2 is known to transport a wide range of purine and pyrimidine nucleosides and nucleobases.

It is expected that inhibition of hENT1 by Rapadocin and its analogs will increase the extracellular concentrations of adenosine, thereby enhancing its signaling via adenosine receptors. Adenosine receptor agonists have been sought as treatments for multiple diseases. It is expected that Rapadocin will have similar activity as adenosine receptor agonists.

As used herein, a "therapeutically effective amount" of a compound, is the quantity of a compound which, when administered to an individual or animal, results in a sufficiently high level of that compound in the individual or animal to cause a discernible inhibition of the ENT1 transporters. The exact dosage and frequency of administration depends on the particular compound of the invention used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines. The invention compounds may be used for the manufacture of a medicine for treatment of a condition or a disease mediated by equilibrative nucleoside transporter ENT1 activity, in particular equilibrative nucleoside transporter ENT1 inhibitory activity.

Equilibrative nucleoside transporter ENT1 mediated conditions or disorders may include but are not limited to acute and chronic pain conditions including inflammatory pain, neuropathic pain, cancer pain, cardioprotection, cerebroprotection, traumatic brain injury (TBI), myeloprotection, neuroprotection, chronic pressure skin ulcers, wound healing, ischemia, anticonvulsant, organ transplant (organ preservation, like cardioplegia), sleep disorders, pancreatitis, glomerulonephritis, and antithrombotic (anti-platelet).

"Nucleoside transport pathways" refer to systems of one or more transport proteins that effect the transport of a substrate across one or more biological membranes. For example, a nucleoside transport pathway may mediate the step-wise transport of a substrate across the plasma membrane followed by the transport of the substrate across the membrane of an intracellular organelle. The transport proteins or nucleoside transporters responsible for such a step-wise translocation of a substrate across two biological membranes may be the same type of nucleoside transporter or may be of different types. In certain embodiments, the nucleoside transporter may be an equilibrative nucleoside transporter. In other embodiments, the nucleoside transporter may be a concentrative nucleoside transporter.

A "transport protein" or "transporter" is a protein that has a direct or indirect role in transporting a molecule across a membrane. The term includes, for example, membrane-bound proteins that recognize a substrate and effects its entry into, or exit from a cell by a carrier-mediated transporter or by receptor-mediated transport. Transporters may be present on plasma membranes or the membranes of intracellular organelles. Thus, transporters facilitate the transport of molecules into the cytoplasm or into an intracellular organelle.

The term "nucleoside" refers to a purine or pyrimidine base that is covalently linked to a 5-carbon sugar (i.e., pentose). When the sugar is ribose, the nucleoside is a ribonucleoside; when it is 2-deoxyribose, the nucleoside is a deoxyribonucleoside. Exemplary nucleosides include cytidine, uridine, adenosine, guanosine, and thymidine, and the corresponding deoxyribonucleosides, which form the basis of the nucleotides that form DNA and RNA.

The term "nucleoside analog" as used herein refers to a nucleoside in which the base moiety, the sugar moiety or both has been modified. Such analogs are generally synthetic and mimic natural nucleosides so that they may take the place of a nucleoside in cellular functions. For example, nucleosides may be incorporated into DNA or RNA in place of the natural corresponding nucleoside. Certain nucleoside analogs so incorporated can, for example, prevent further elongation of the nucleic acid chain during synthesis. Many nucleoside analogs have anti-viral or anti-cancer properties. Examples of nucleoside analogs include inosine, deoxyadenosine analogs such as didanosine (2',3'-dideoxyinosine, ddI) and vidarabine (9-O-D-ribofuranosyladenine), deoxycytidine analogs such as cytarabine (cytosine arabinoside, emtricitabine, lamivudine (2',3'-dideoxy-3'-thiacytidine, 3TC), and zalcitabine (2'-3'-dideoxycytidine, ddC), deoxyguanosine analogs such as abacavir, (deoxy-)thymidine analogs such as stavudine (2'-3'-didehydro-2'-3'-dideoxythymidine, d4T) and zidovudine (azidothymidine, or AZT), and deoxyuridine analogs such as idoxuridine and trifluridine.

The term "pharmaceutically acceptable salts" refers to physiologically and pharmaceutically acceptable salts of the compounds of the invention, e.g., salts that retain the desired biological activity of the parent compound and do not impart undesired toxicological effects thereto.

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

Example 1

Rapadocin Inhibits Nucleoside Uptake

Figure 2:
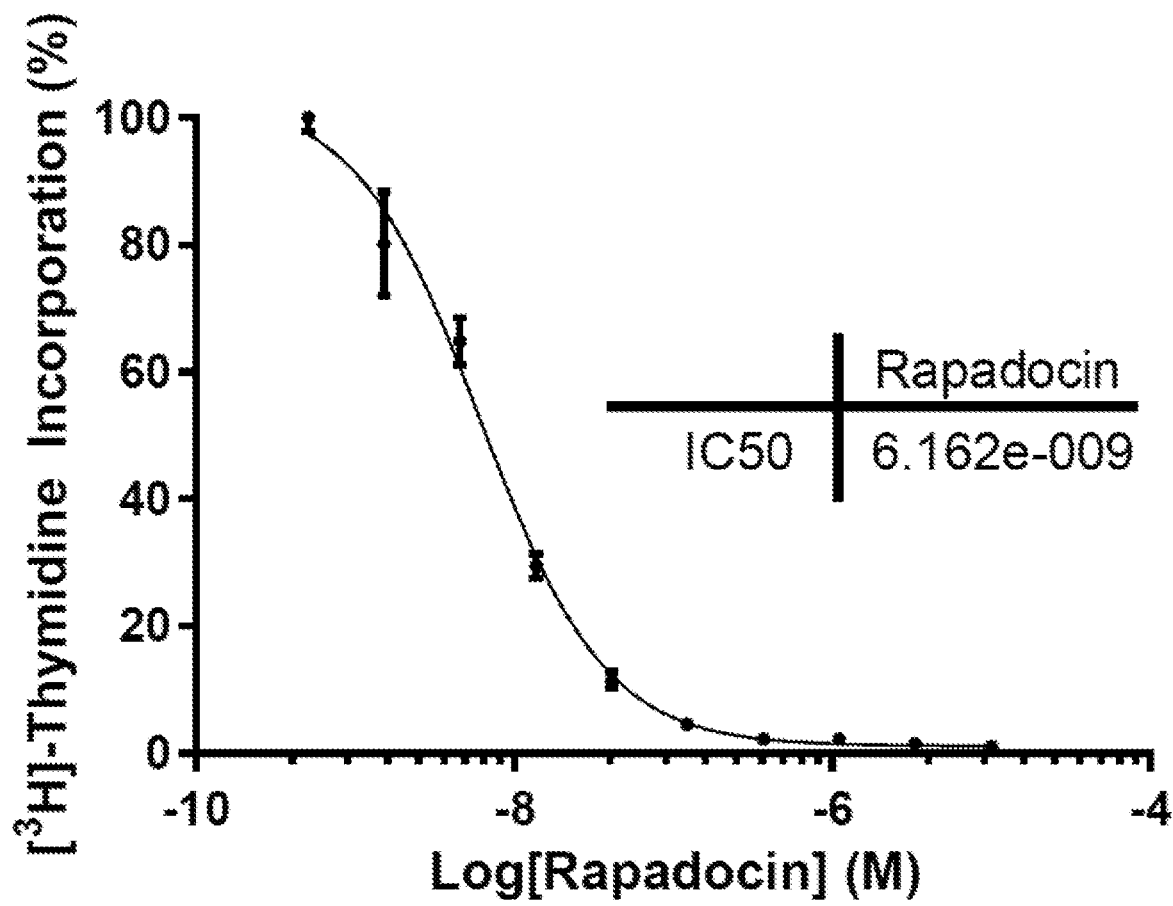
FIG. 2. Rapadocin inhibits $^3$H-Thymidine uptake in Human Umbilical Vein Endothelial Cells (HUVEC).
Figure 3:
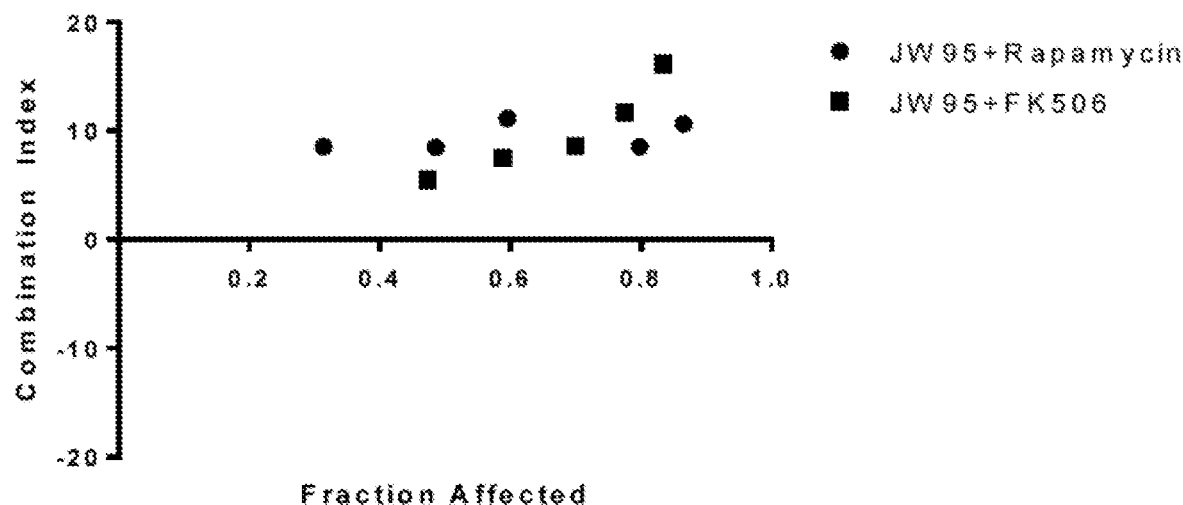
FIG. 3. Rapadocin's uptake inhibition is antagonized by FKBP12-binders Rapamycin and FK506.

Rapadocin potently and specifically inhibits nucleoside uptake by human equilibrative nucleoside uptake transporter 1 (hENT1) over hENT2, the two most predominant eqilibrative nucleoside transporters (FIG. 1). Rapadocin inhibits nucleoside uptake in at least seven cell lines and is predicted to inhibit nucleoside uptake in all human cell lines (see e.g., FIG. 2 and Table 1).

TABLE 1

$^3$H-Thymidine Uptake in Various Cell Lines

| | HUVEC | 293T | RKO | A549 | HeLa | MCF-7 | MDA MB-231 |
|---|---|---|---|---|---|---|---|
| EC50 | 6.4 nM | 5.0 nM | 11.4 nM | 6.3 nM | 16.3 nM | 9.0 nM | 41.1 nM |

Rapafucin Analogs

TABLE 2

| | Peptide | | | | EC$_{50}$ $^3$H-Tymidine |
|---|---|---|---|---|---|
| Analog | Residue 1 | Residue 2 | Residue 3 | Residue 4 | uptake |
| JW95-1 | mGly | dPro | mGly | Phe | >1 uM |
| JW95-2 | mAla | dPro | mGly | Phe | >1 uM |
| JW95-3 | mLeu | dPro | mGly | Phe | >1 uM |
| JW95-4 | mSer | dPro | mGly | Phe | 1228 |
| JW95-5 | mPhe | dPro | mGly | Phe | 440 |
| JW95-6 | mGly | dPro | mAla | Phe | >1 uM |
| JW95-7 | mAla | dPro | mAla | Phe | >1 uM |
| JW95-8 | mLeu | dPro | mAla | Phe | >1 uM |
| JW95-9 | mSer | dPro | mAla | Phe | >1 uM |
| JW95-10 | mPhe | dPro | mAla | Phe | >1 uM |
| JW95-11 | mGly | dPro | mLeu | Phe | >1 uM |
| JW95-12 | mAla | dPro | mLeu | Phe | >1 uM |

TABLE 2-continued

| Analog | Peptide | | | | EC$_{50}$ $^3$H-Tymidine uptake |
| --- | --- | --- | --- | --- | --- |
| | Residue 1 | Residue 2 | Residue 3 | Residue 4 | |
| JW95-13 | mLeu | dPro | mLeu | Phe | 787 |
| JW95-14 | mSer | dPro | mLeu | Phe | 725 |
| JW95-15 | mPhe | dPro | mLeu | Phe | 377 |
| JW95-16 | mGly | dPro | mSer | Phe | >1 uM |
| JW95-17 | mAla | dPro | mSer | Phe | >1 uM |
| JW95-18 | mLeu | dPro | mSer | Phe | >1 uM |
| JW95-19 | mSer | dPro | mSer | Phe | >1 uM |
| JW95-20 | mPhe | dPro | mSer | Phe | >1 uM |
| JW95-21 | mGly | dPro | mPhe | Phe | >1 uM |
| JW95-22 | mAla | dPro | mPhe | Phe | 731 |
| JW95-23 | mLeu | dPro | mPhe | Phe | >1 uM |
| JW95-24 | mSer | dPro | mPhe | Phe | >1 uM |
| JW95-25 | mPhe | dPro | mPhe | Phe | >1 uM |
| 95-15-1 | mLeu | dPro | mPhe | Phe | 112 |
| 95-15-2 | mdLeu | dPro | mPhe | Phe | >1 uM |
| 95-15-3 | mLeu | dPro | mPhe | dhoPhe | >1 uM |
| 95-15-4 | Leu | dPro | mPhe | Phe | >1 uM |
| 95-15-5 | mIle | dPro | mPhe | Phe | >1 uM |
| 95-15-6 | mNle | dPro | mPhe | Phe | >1 uM |
| 95-15-7 | mLeu | Pro | mPhe | Phe | >1 uM |
| 95-15-8 | mLeu | Gly | mPhe | Phe | >1 uM |
| 95-15-9 | mLeu | dPro | mdPhe | Phe | >1 uM |
| 95-15-10 | mLeu | dPro | Phe | Phe | 182 |
| 95-15-11 | mLeu | dPro | mPhe | dPhe | >1 uM |
| 95-15-12 | mLeu | dPro | mPhe | hoPhe | >1 uM |
| 95-15-13 | mLeu | dPro | mPhe | Phg | 15 |
| 95-15-14 | mLeu | dPro | mPhe | PheF | >1 uM |
| 95-15-15 | mLeu | dPro | mPhe | PheCl | >1 uM |
| 95-15-16 | mLeu | dPro | mPhe | PheI | >1 uM |
| 95-15-17 | mLeu | dPro | mPhe | Tyr | >1 uM |
| 95-15-18 | mLeu | dPro | mPhe | TyrBu | >1 uM |
| 95-15-19 | mLeu | dPro | mPhe | PheNO2 | >1 uM |
| 95-15-20 | mLeu | dPro | mPhe | mPhe | >1 uM |
| 95-15-21 | mLeu | dPro | mPhe | Cha | 112 |
| 95-15-22 | mLeu | dPro | mPhe | NaI | >1 uM |
| 95-15-23 | mLeu | dPro | mPhe | biPhe | >1 uM |
| Rapadocin | mLeu | dPro | mPhe | Phg | 6.16 |
| 95-15-13-2 | mLeu | dHoPro | mPhe | Phg | 1920 |
| 95-15-13-3 | mLeu | dPro | Phe | Phg | 64 |
| 95-15-13-4 | mLeu | dPro | Pyr | Phg | 266 |
| 95-15-13-5 | mLeu | dPro | hoPhe | Phg | 15 |
| 95-15-13-6 | mLeu | dPro | Phg | Phg | 261 |
| 95-15-13-7 | mLeu | dPro | PheF | Phg | 56.7 |
| 95-15-13-8 | mLeu | dPro | PheCl | Phg | 123 |
| 95-15-13-9 | mLeu | dPro | PheI | Phg | 62.5 |
| 95-15-13-10 | mLeu | dPro | Tyr | Phg | 9.64 |
| 95-15-13-11 | mLeu | dPro | TyrOMe | Phg | 32.6 |
| 95-15-13-12 | mLeu | dPro | PheNO2 | Phg | 130 |
| 95-15-13-13 | mLeu | dPro | Cha | Phg | 199 |
| 95-15-13-14 | mLeu | dPro | Nal | Phg | 87.8 |
| 95-15-13-15 | mLeu | dPro | biPhe | Phg | 194 |
| JW95Diol[1] Formula II | mLeu | dPro | mPhe | Phg | 3 |
| JW95TyrBiotin Formula III | mLeu | dPro | Tyr(PEG)2Biotin | Phg | 64 |
| JW95S2Biotin | mLeu | dPro | mPhe | Phg | >1 uM |
| JW95TyrDiaz Formula IV | mLeu | dPro | Tyr---Diaz | Phg | 20 nM |

[1]JW95Diol utilizes a modified FKBD where the two methoxy groups are replaced with hydroxyl groups Table 2 discloses the potency of various Rapadocin analogs.
Structures of selected Rapadocin analogs are represented as follows:
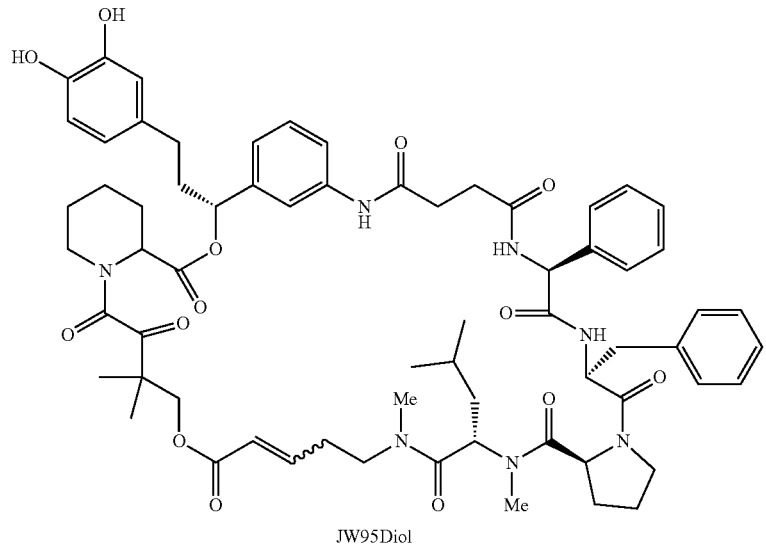
JW95Diol
Formula II
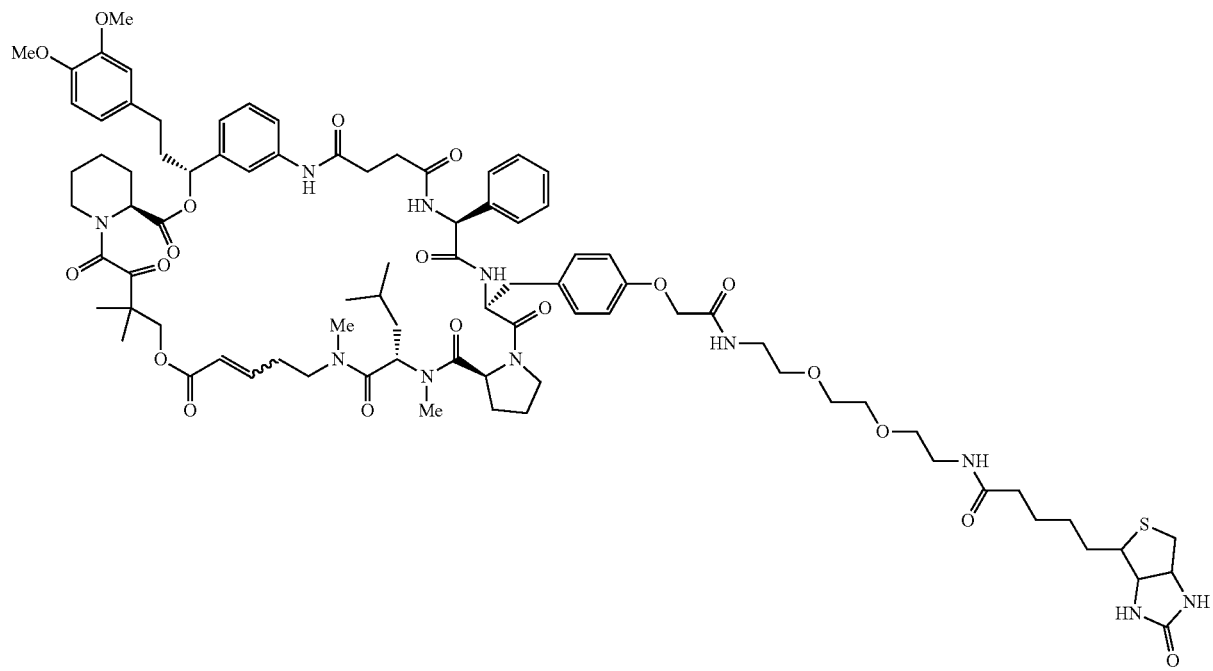
JW95TyrBiotin
Formula III -continued

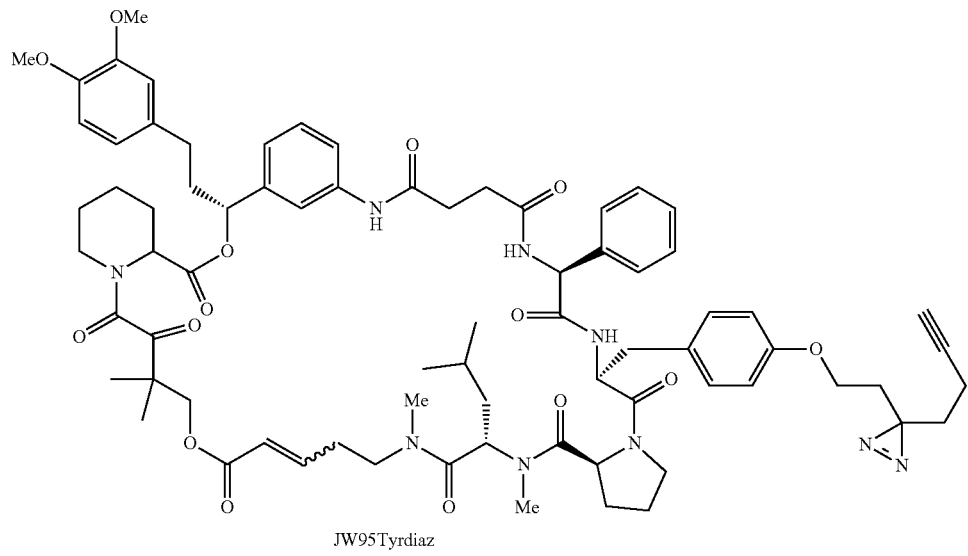

Formula IV

JW95Tyrdiaz

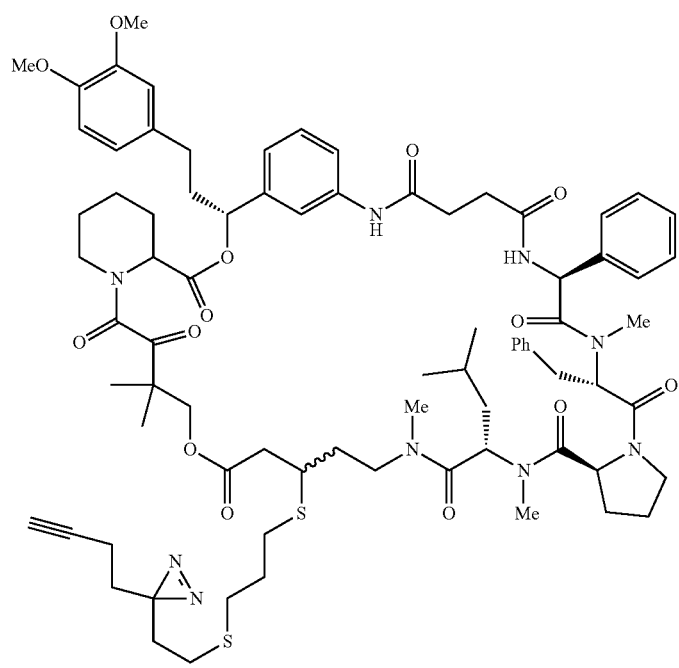

Formula V

JW95-S2-diaz

Example 2

Human and Animal Models

Figure 4:
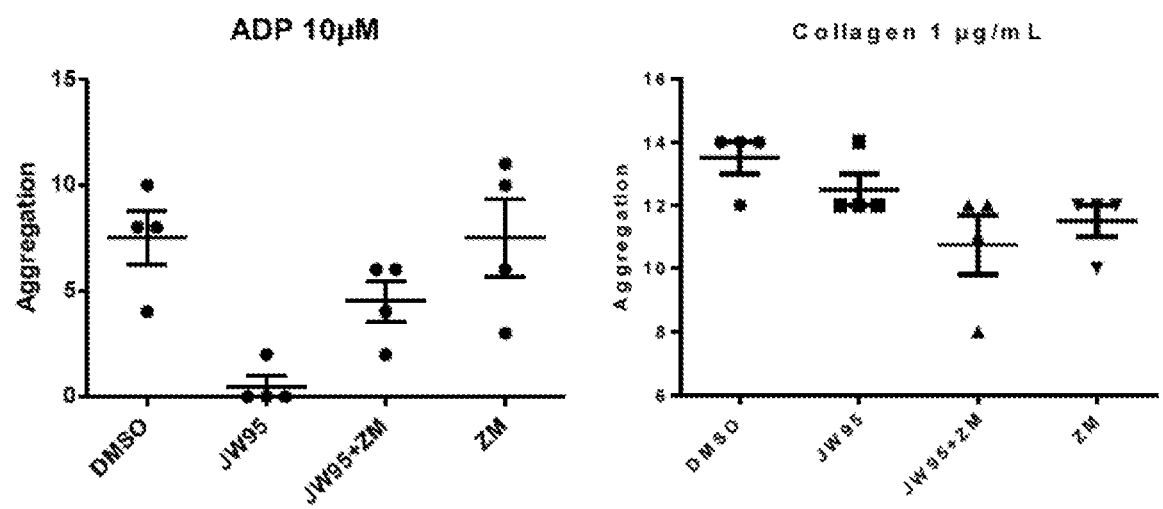
FIG. 4. 5 Rapadocin inhibits platelet aggregation in human blood when activated by ADP.
Figure 5:
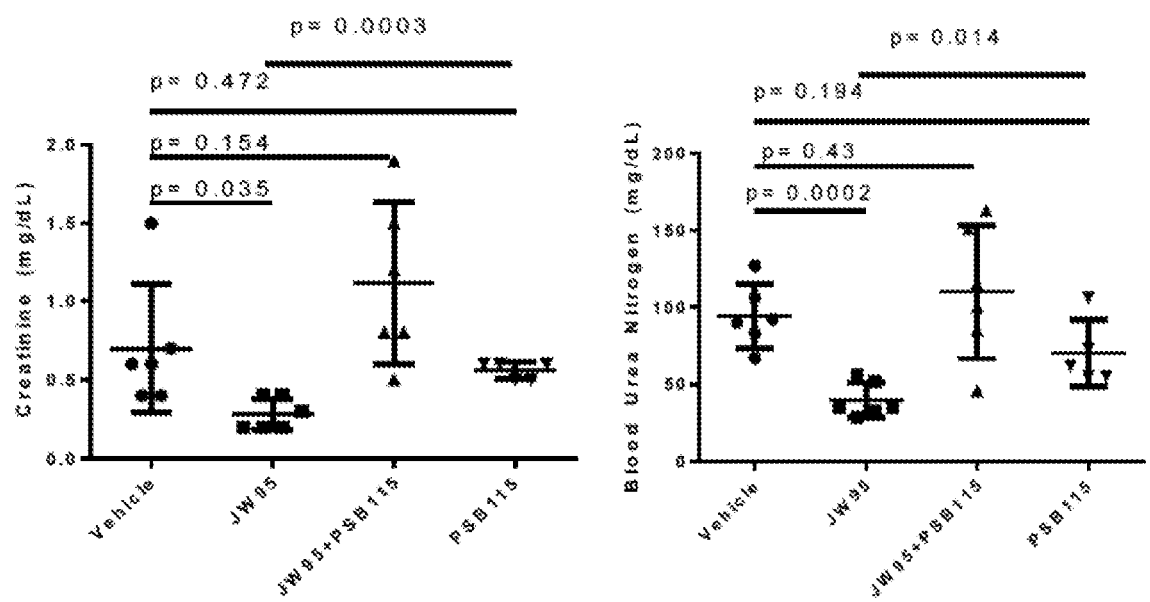
FIG. 5. Rapadocin protects against kidney ischemia reperfusion injury in a mouse model.

Two human and animal models have been studied to show the efficacy of Rapadocin (FIGS. 4 and 5). Under several physiological conditions, adenosine is released into the blood where it can act on adenosine receptors. Normally, this adenosine (ADO) is rapidly reabsorbed via ENT1. In the presence of Rapadocin, uptake is inhibited and ADO is able to produce enhanced signaling leading to several potentially beneficial physiological responses.

Example 3
Additional compounds that can be used to improve Pharmacokinetics/Pharmacodynamics and solubility of the leads include the following:
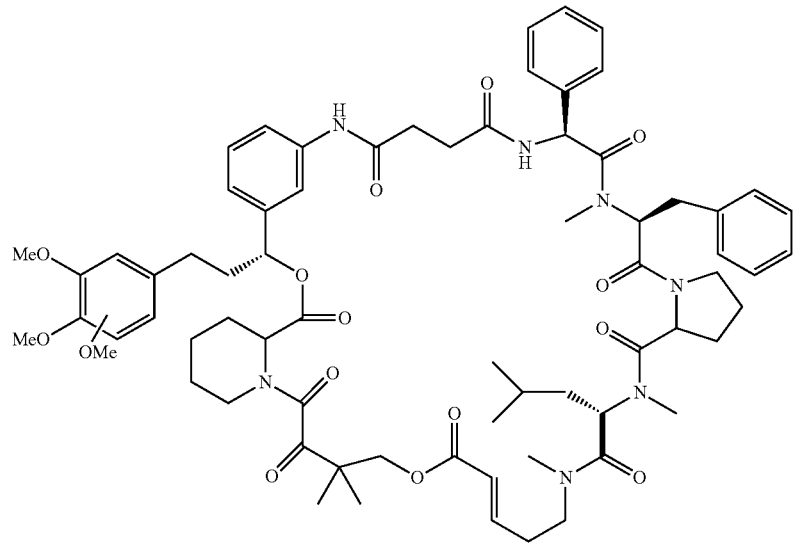
Formula VI
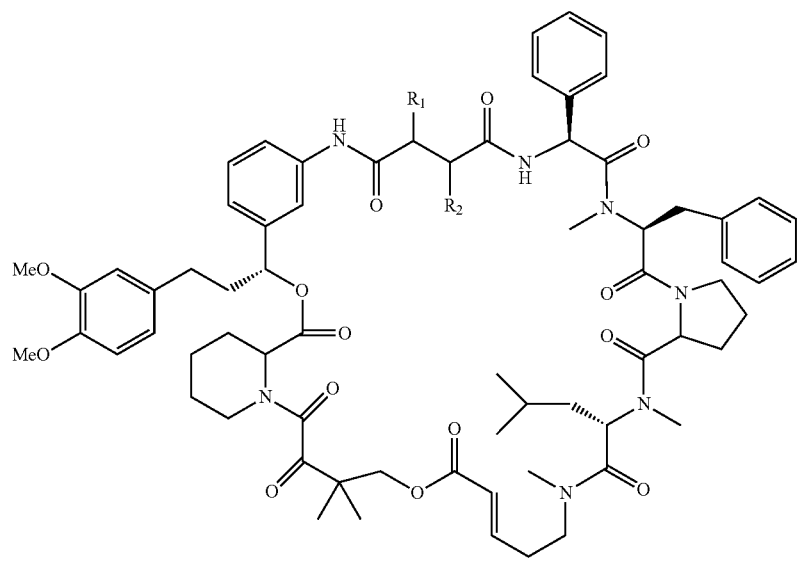
Formula VII
($R_1$ = OH, $NH_2$, SH, H;
$R_2$ = OH, $NH_2$, SH, H)

Formula VIII
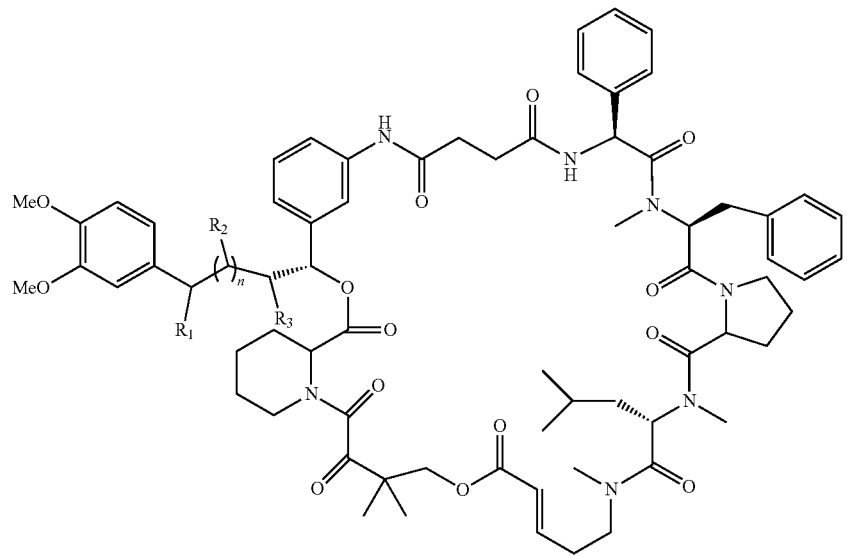
n = 0-6
R₁-R₃: individually or in combination, = methyl, ethyl, propyl, isopropyl, phenyl, OH, NH₂, SH.
Formula IX
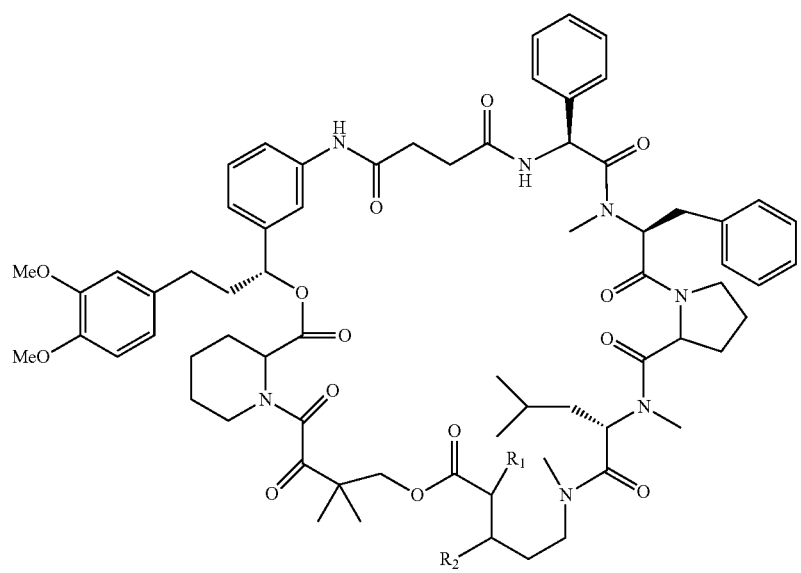
(R₁ = OH, NH₂, SH, H;
R₂ = OH, NH₂, SH, H)

Formula X
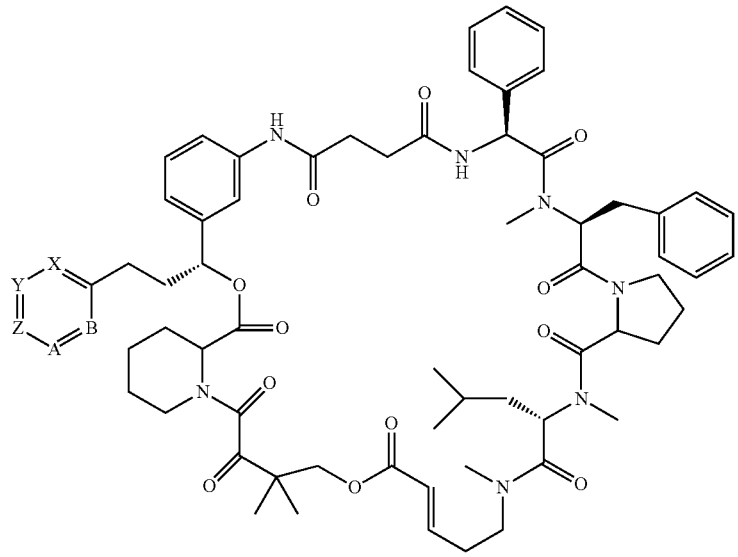
A = B = X = Y = Z = C;
A, B, X, Y, Z = N, P;
A = B = N, X = Y = Z = H;
X = Z = N, Y = A = B = H;
X = A = N, Y = Z = B = H;
X = Y = Z = N, A = B = H;
X = Y = Z = A = N, B = H;
Formula XI
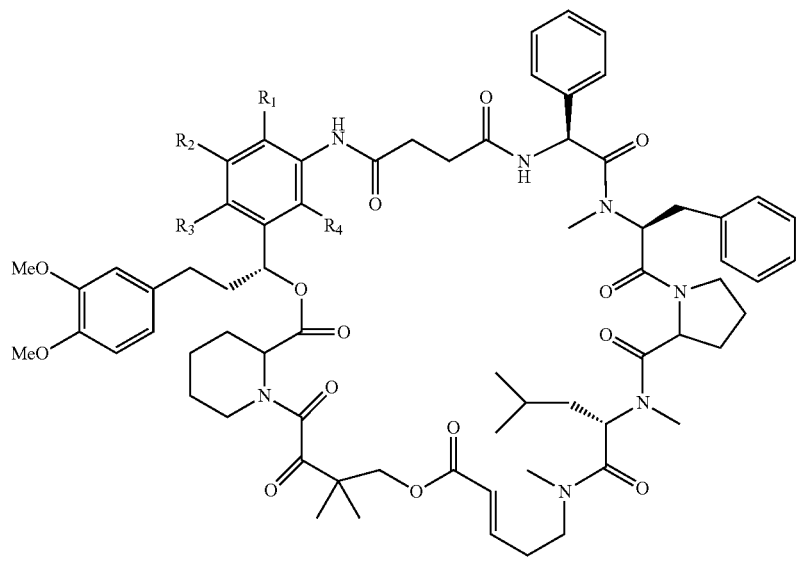
$R_1$-$R_4$: individually or in combination, = methyl,
ethyl, propyl, isopropyl, phenyl,
OH, $NH_2$, SH.

Formula XII
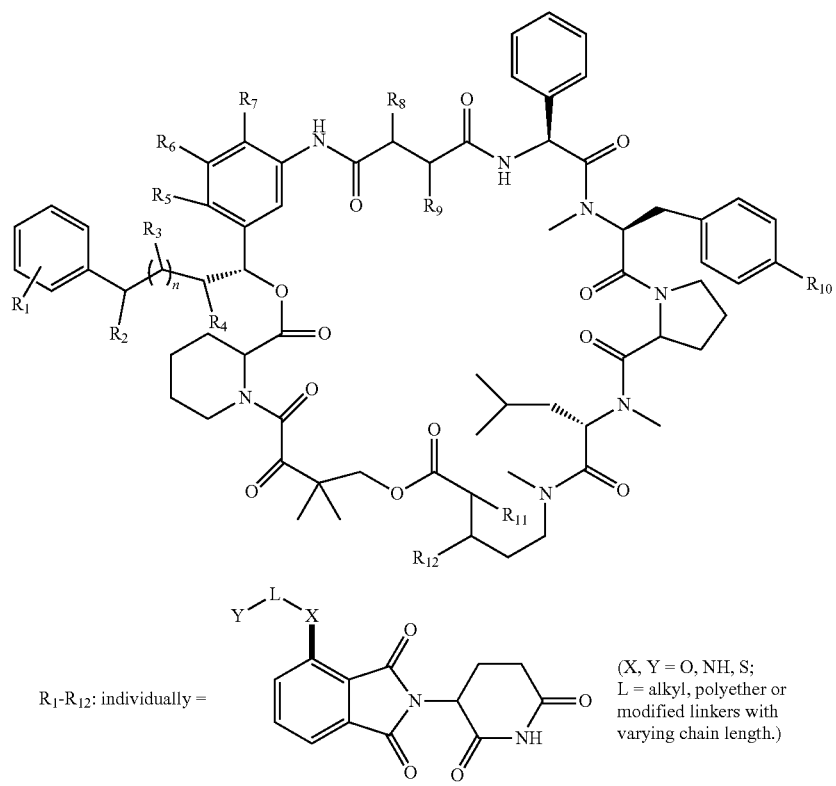
$R_1-R_{12}$: individually =
(X, Y = O, NH, S; L = alkyl, polyether or modified linkers with varying chain length.)
Example 4
Scheme 1
Synthetic route for Rapadocin with FKBD 8
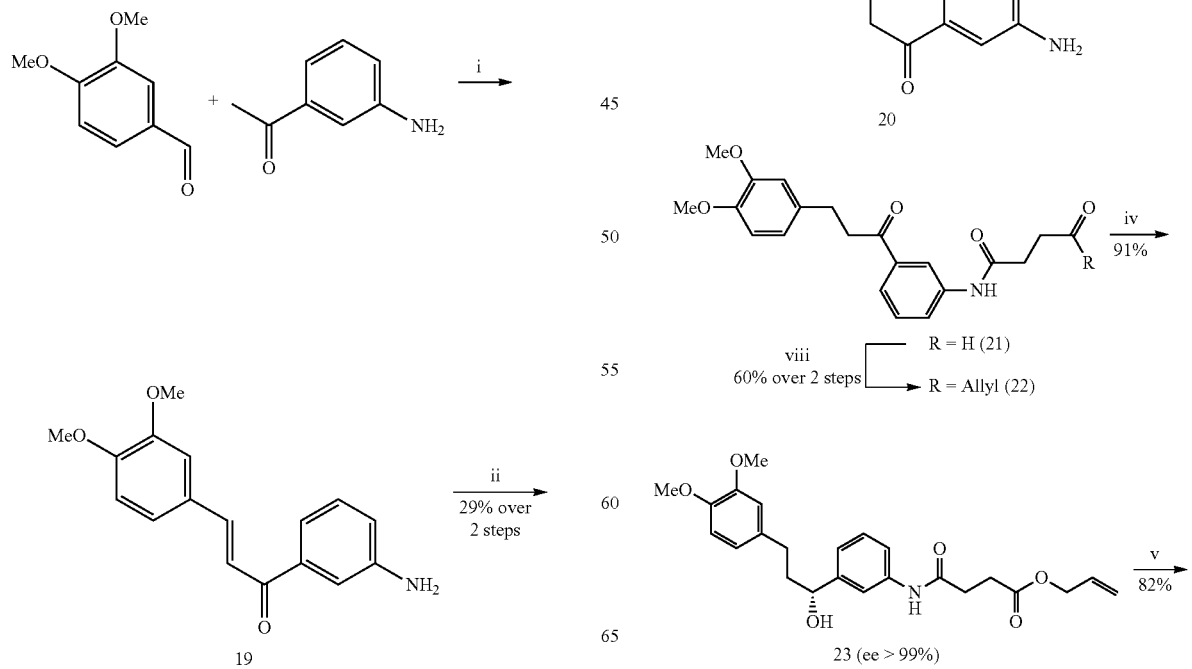

-continued

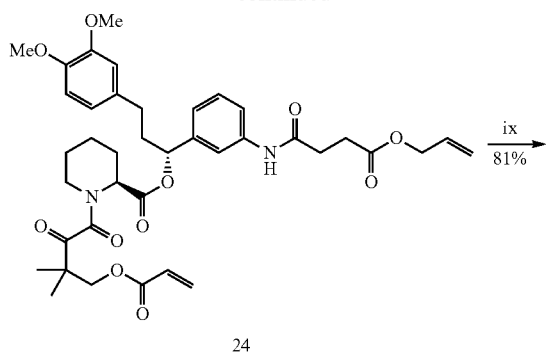

24

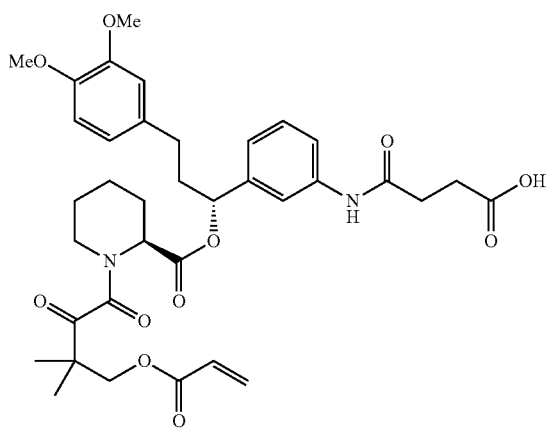

11

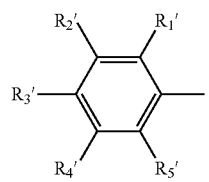

8

Reaction conditions: i) KOH, H$_2$O/EtOH (1/20), RT, 6 h; ii) Pd/C (10%), H$_2$, MeOH, RT, 1.5 h; iii) tert-butyl 2-bromoacetate, K$_2$CO$_3$, DMF/acetone (1/2), RT, 4 h; iv) (+)-DIPCl, THF, −20° C. to RT, 5 h; v) FKBD 8, benzoyl chloride, DMAP (5%), NEt$_3$, CH$_2$Cl$_2$, RT, 4 h; vi) TFA (10%), CH$_2$Cl$_2$, RT, 6 h; vii) succinic anhydride, DMAP (5%), CH$_2$Cl$_2$, RT, 3 h; viii) allyl bromide, Cs$_2$CO$_3$, DMF, RT, 2 h; ix) Pd(PPh$_3$)$_4$ (10%), N-methylaniline, THF, RT, 6 h.

Example 5

Compounds that can be used to improve Pharmacokinetics/Pharmacodynamics and solubility are represented by the following generic structure:

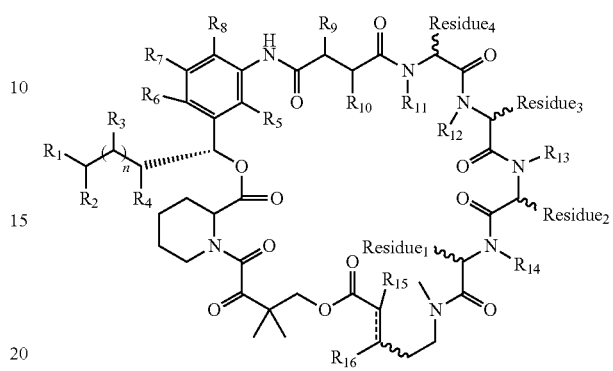

n=0-6
R$_1$:

Wherein R$_1$'-R$_5$'=OH, NH$_2$, SH, CN, H, OAc, or OMe individually or in combination.

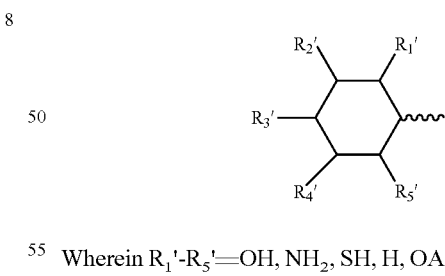

Wherein: A, B, X, Y, Z=C, N, or P either individually or in combination.

Wherein R$_1$'-R$_5$'=OH, NH$_2$, SH, H, OAc, OMe individually or in combination.

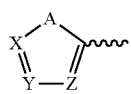

Wherein A, X, Y, or Z=CH$_n$' (n'=0-2), O, N, S, wherever appropriate, individually or in combination.
R$_2$-R$_4$: H, methyl, ethyl, propyl, isopropyl, phenyl, OH, NH$_2$, SH, CN, individually or in combination.

$R_5-R_8$: methyl, ethyl, propyl, isopropyl, phenyl, OH, $NH_2$, SH, CN, individually or in combination.

$R_9$=OH, $NH_2$, SH, CN, H;

$R_{10}$=OH, $NH_2$, SH, CN, H.

$R_{11-14}$=H or Me.

$R_{15}$=OH, $NH_2$, SH, CN, H;

$R_{16}$=OH, $NH_2$, SH, CN, H.

The bond between the carbons bearing $R_{15}$ and $R_{16}$ can be either a single or a double bond in either E or Z configuration.

Residues 1-4 can be any amino acid building block listed in Table 3 or its modified version.

TABLE 3

Amino Acid Building Blocks for Residues in the Effector Domain

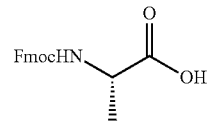

Ala

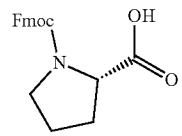

Pro

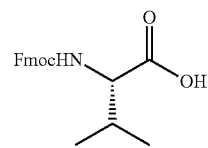

Val

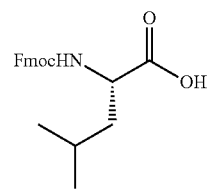

Leu

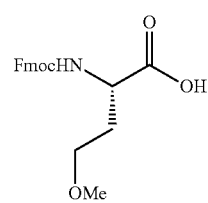

HoSerMe

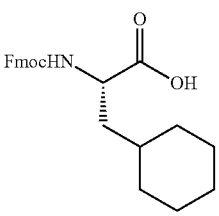

ChA

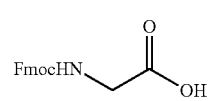

Gly

TABLE 3-continued

Amino Acid Building Blocks for Residues in the Effector Domain

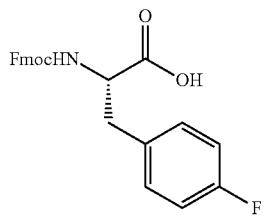

PhF

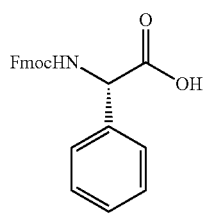

PhG

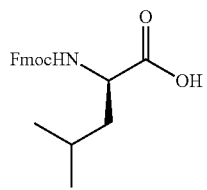

dLeu

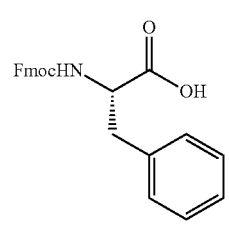

Phe

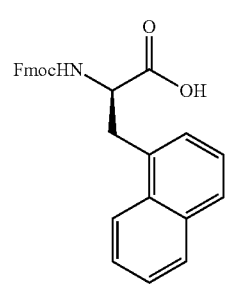

Nal

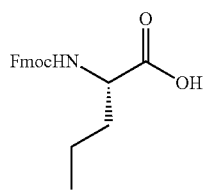

Nva

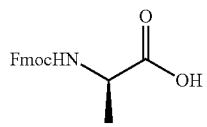

dAla

TABLE 3-continued

Amino Acid Building Blocks for Residues in the Effector Domain

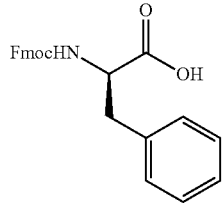
dPhe

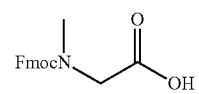
mGly

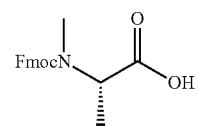
mAla

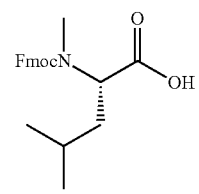
mLeu

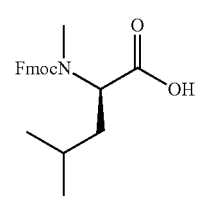
mdLeu

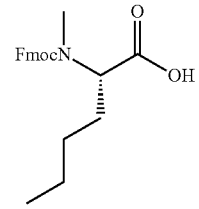
mNle

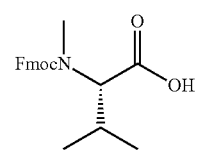
mVal

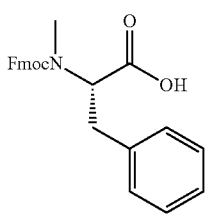
mPhe

TABLE 3-continued

Amino Acid Building Blocks for Residues in the Effector Domain

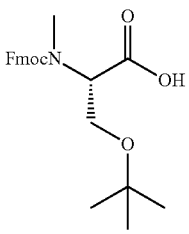
mSerBu

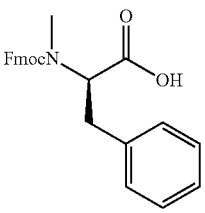
mdPhe

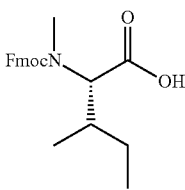
mIle

References 11-15 describe the use of adenosine agonists in the treatment of various diseases. Based upon the information disclosed in these references, one of ordinary skill in the art would recognize that the compounds disclosed in this application could be used to treat these diseases. See e.g., Table 2 of Reference 15 as it relates to the treatment of arrhythmias.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

REFERENCES

The following references are each relied upon and incorporated herein in their entirety.
1. Passer, B. J. et al. Identification of the ENT1 Antagonists Dipyridamole and Dilazep as Amplifiers of Oncolytic Herpes Simplex Virus-1 Replication. *Cancer Res.* 70, 3890-3895 (2010).
2. Köse, M. & Schiedel, A. C. Nucleoside/Nucleobase Transporters: Drug Targets of the Future? *Future Med. Chem.* 1, 303-326 (2009).
3. Melendez, R. I. and Kalivas, P. W. Last Call for Adenosine Transporters. *Nat. Neurosci.* 7, 795-796 (2004).
4. Choi, D.-S. et al. The Type 1 Equilibrative Nucleoside Transporter Regulates Ethanol Intoxication and Preference. *Nat. Neurosci.* 7, 855-861 (2004).
5. Puetz, C. et al. Nitrobenzylthioinosine Compounds for Relief of Pain. (Google Patents, 2008) at www.google.com/patents/U.S. Pat. No. 7,358,235.
6. Sawynok, J. in *Adenosine* 343-360 (Springer, 2013) at link.springer.com/chapter/10.1007/978-1-4614-3903-5_17.

7. Bauerle, J. D., Grenz, A., Kim, J.-H., Lee, H. T. and Eltzschig, H. K. Adenosine Generation and Signaling during Acute Kidney Injury. *J Am. Soc. Nephrol.* 22, 14-20 (2011).
8. Grenz, A. et al. The Reno-Vascular A2B Adenosine Receptor Protects the Kidney from Ischemia. *PLoS Med.* 5, e137 (2008).
9. Grenz, A. et al. Equilibrative Nucleoside Transporter 1 (ENT1) Regulates Postischemic Blood Flow during Acute Kidney Injury in Mice. *J. Clin. Invest.* 122, 693-710 (2012).
10. Zimmerman, M. A. et al. Equilibrative Nucleoside Transporter (ENT)-1-Dependent Elevation of Extracellular Adenosine Protects the Liver during Ischemia and Reperfusion. *Hepatology* 58, 1766-1778 (2013).
11. Mohamadnejad, M. et al. Adenosine Inhibits Chemotaxis and Induces Hepatocyte-Specific Genes in Bone Marrow Mesenchymal Stem Cells. *Hepatology* 51(3), 963-73 (2010).
12. Wen, J. et al. Adenosine Signaling: Good or Bad in Erectile Function? *Arterioscler. Thromb. Vasc. Biol.* 32(4), 845-50 (2012).
13. Xu, Z. et al. ENT1 Inhibition Attenuates Epileptic Seizure Severity Via Regulation of Glutamatergic Neurotransmission. *Neuromolecular Med.* 17(1), 1-11 (2015).
14. Chen, J. et al. Adenosine Receptors as Drug Targets-What are the Challenges? *Nat. Rev. Drug Disc.* 12(4), 265-86 (2013).
15. Sachdeva, S. et al. Adenosine and its Receptors as Therapeutic Targets: An Overview. *Saudi Pharm. J* 21, 245-253 (2013).
16. Griffith et al. *Biochim. Bioph. Acta* 1286:153-181 (1986).
17. Lu X. et al., *J. Exp. Ther. Oncol.* 2:200-212, 2002.
18. Pennycooke M. et al. *Biochem. Biophys. Res. Commun.* 208, 951-959, 2001.

What is claimed is:

1. A compound with the following formula:

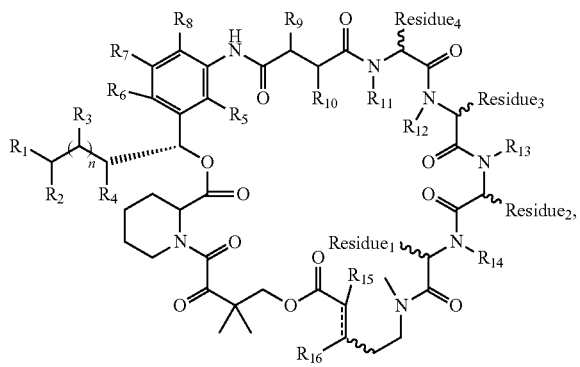

wherein
n is an integer selected from 0 to 6;
$R_1$ is selected from the group consisting of

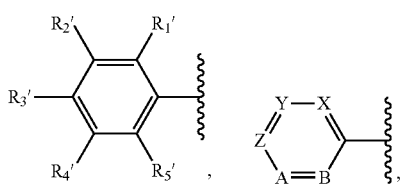

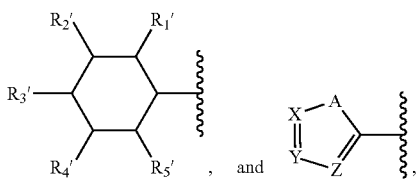

when $R_1$ is

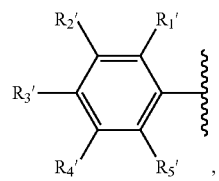

each $R_1'$, $R_2'$, $R_3'$, $R_4'$, and $R_5'$ is independently selected from the group consisting of OH, $NH_2$, SH, CN, H, OAc, and OMe,
when $R_1$ is

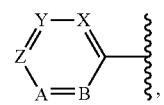

each A, B, X, Y, and Z is independently C or N,
when $R_1$ is

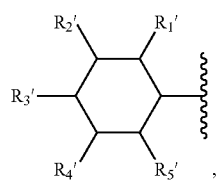

each $R_1'$, $R_2'$, $R_3'$, $R_4'$, and $R_5'$ is independently selected from the group consisting of OH, $NH_2$, SH, H, OAc, and OMe,
when $R_1$ is

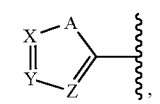

each A, X, Y, and Z is independently selected from the group consisting of —(CH)m-, O, N, and S, m is an integer selected from 0 to 2;
each $R_2$, $R_3$, and $R_4$ is independently selected from the group consisting of H, methyl, ethyl, propyl, isopropyl, phenyl, OH, $NH_2$, SH, and CN;
each $R_5$, $R_6$, $R_7$, and $R_8$ is independently selected from the group consisting of methyl, ethyl, propyl, isopropyl, phenyl, OH, $NH_2$, SH, and CN;
each $R_9$ and $R_{10}$ is independently selected from the group consisting of OH, $NH_2$, SH, CN, and hydrogen;
each $R_{11}$, $R_{12}$, $R_{13}$, and $R_{14}$ is independently selected from the group consisting of hydrogen and methyl;
each $R_{15}$ and $R_{16}$ is independently selected from the group consisting of OH, $NH_2$, SH, CN and hydrogen;

"═" represents a single bond or a double bond with E or Z configuration; and
the amino acids with residues 1 to 4 are selected from the group consisting of
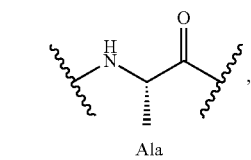
Ala
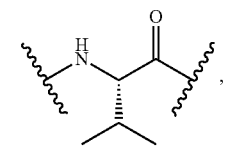
Val
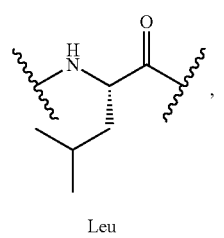
Leu
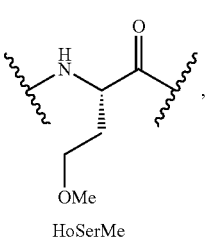
HoSerMe
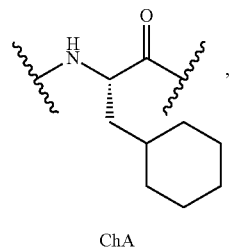
ChA
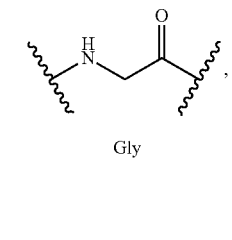
Gly
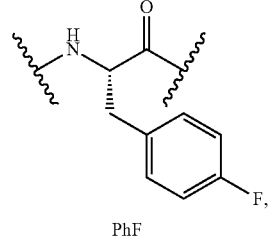
PhF
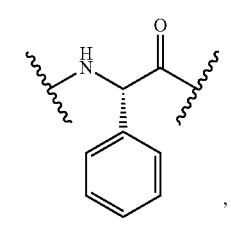
PhG
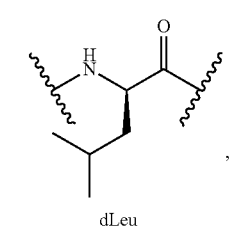
dLeu
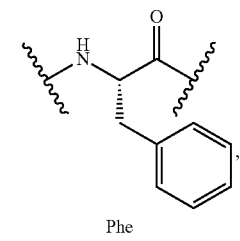
Phe
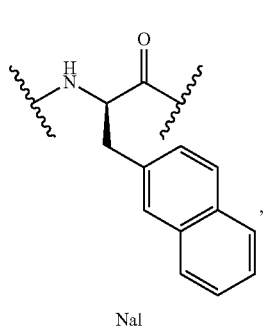
Nal
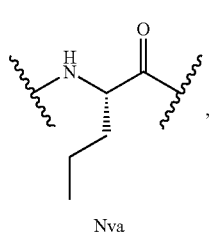
Nva
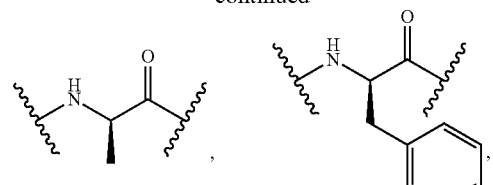
dAla, dPhe
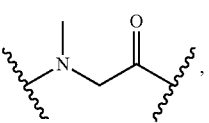
mGly
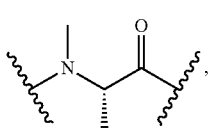
mAla
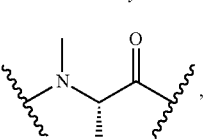
mLeu
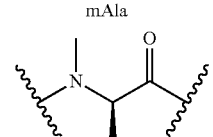
mdLeu
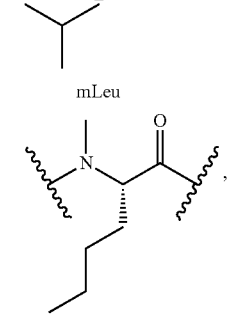
mNle
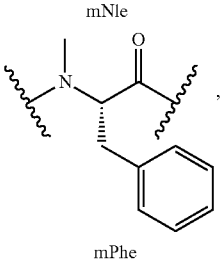
mPhe
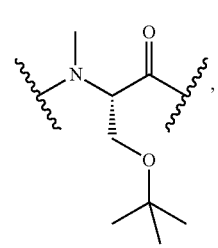
mSerBu
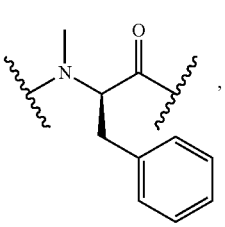
mdPhe
and
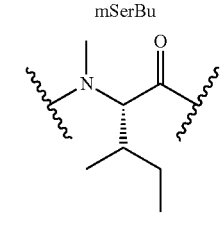
mIle,
or residue 1, 2, 3, or 4 and the adjacent nitrogen form
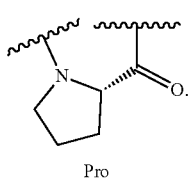 [SMILES: *C(=O)[C@@H]1CCCN1*]
Pro 2. A pharmaceutical composition comprising the compound of claim 1 and a pharmaceutically acceptable carrier.

3. The pharmaceutical composition of claim 2, wherein the composition is in a dosage form suitable for oral administration, rectal administration, percutaneous administration or parenteral injection.

* * * * *